(12) United States Patent
Aiken et al.

(10) Patent No.: US 8,337,902 B2
(45) Date of Patent: Dec. 25, 2012

(54) DEGRADATION OF PRION PROTEIN AND REDUCED PRION INFECTIVITY BY EARTHWORM HOMOGENATES

(75) Inventors: Judd M. Aiken, Edmonton (CA); Jay R. Schneider, Mount Horeb, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/566,406

(22) Filed: Sep. 24, 2009

(65) Prior Publication Data

US 2010/0074962 A1    Mar. 25, 2010

Related U.S. Application Data

(60) Provisional application No. 61/099,944, filed on Sep. 25, 2008.

(51) Int. Cl.
*A61K 35/12* (2006.01)
*A61K 35/32* (2006.01)
*A61K 35/34* (2006.01)

(52) U.S. Cl. .................... 424/520; 424/548; 424/574
(58) Field of Classification Search .................. None
See application file for complete search history.

(56) References Cited

U.S. PATENT DOCUMENTS

| 5,024,844 | A | 6/1991 | Ishii et al. |
| 7,393,818 | B2 | 7/2008 | McDonnel et al. |
| 7,399,603 | B2 | 7/2008 | Zheng et al. |
| 7,407,760 | B2 | 8/2008 | Supattapone et al. |
| 2008/0069857 | A1* | 3/2008 | Yeo et al. ............... 424/426 |
| 2008/0206843 | A1* | 8/2008 | Croud et al. ............ 435/264 |
| 2010/0311769 | A1* | 12/2010 | Cho et al. ............ 514/266.21 |

FOREIGN PATENT DOCUMENTS

| EP | 1522354 | * | 4/2005 |
| WO | WO 2006/119060 | * | 11/2006 |

OTHER PUBLICATIONS

Nechitaylo, T. The role of earhworm gut-associated microorganisms in the fate of prions in soil. Jan. 2007. Avail. Metadata on Internet Documents, Order No. 372435; From: Metadata Internet Doc. [German Dissertation] (D1030-1), 100 pages.*

Laino, C. Enzyme Found to Degrade Prions. Neurology Today. Mar. 2004. vol. 4, No. 3, 5-page article.*

Website publication entitled Prionzyme (TM). Prion removal. Powerful. Pracdtical. Proven. 2006 (www.genencor.com), downloaded from http://bio4eu.jrc.ec.europa.eu/documents/PrionzymeBackgrounderfinal.pdf; 6-page document.*

Cho, Il Hwan et al., Purification and characterization of six fibrinolytic serine-proteases from earthworm *Lumbricus rubellus*, *Journal of Biochemistry and Molecular Biology*, 37(2):199-205, Mar. 2004.

Hrzenjak, Terezija et al., Fibrinolytic and anticoagulative activities from the earthworm *Eisenia foetida*, *Comparative Biochemistry and Physiology*, Part B 119:825-832, 1998.

Nakajima, Nobuyoshi et al., Characterization of potent fibrinolytic enzymes in earthworm, *Lumbricus rubellus*, *Biosci. Biotech. Biochem.*, 57(10):1726-1730, 1993.

Park, Yong-Doo et al., Rapid purification and biochemical characteristics of lumbrokinase III from earthworm for use as a fibrinolytic agent, *Biotechnology Letters*, 20(2):169-172, Feb. 1998.

Schneider et al., Degradation of prion protein by earthworm fibrinolytic enzyme, Epidemiology, Risk Assessment and Transmission, EICC, Edinburgh, Scotland, UK, Sep. 26-28, 2007, www.prion2007.com, p. 04-68.

Sumi, Hiroyuki et al., A very stable and potent fibrinolytic enzyme found in earthworm *Lumbricus rubellus* autolysate, *Comp. Biochem. Physiol.*, 106B(3):763-766, 1993.

Wang, Feng et al., Crystal structure of earthworm fibrinolytic enzyme component B: a novel, glycosylated two-chained trypsin, *J. Mol. Bio.*, 348:671-685, 2005.

Wang, Feng et al., Purification, characterization and crystallization of a group of earthworm fibrinolytic enzymes from *Eisenia fetida*, *Biotechnology Letters*, 25L1105-1109, 2003.

Wang, Xue-Qing et al., An earthworm protease cleaving serum fibronectin and decreasing HBeAg in HepG2.2.15 cells, *BMC Biochemistry*, 9:30, 2008.

Wu, Jin Xia et al., Glycosylated trypsin-like proteases from earthworm *Eisenia fetida*, *International Journal of Biological Macromolecules*, 40:399-406, 2007.

Yang, Jia-Shu and Ru, Bing-Gen, Purification and characterization of an SDS-Activated fibrinolytic enzyme from *Eisenia fetida*, *Comp. Biochem. Physiol.*, 118B(3):623-631, 1997.

Zhao, Jing et al., *Eisenia fetida* protease-III-1 functions in both fibrinolysis and fibrogenesis, *Journal of Biomedicine and Biotechnology*, 2007, Article ID 97654, pp. 1-10.

Zhou, Jing et al., Assay of lumbrokinase with a chromophoric substrate, *Protein and Peptide Letters*, 4(6):409-414, 1997.

Caughey, Byron et al., "Getting a grip on prions: oligomers, amyloids and pathological membrane interactions", National Institute of Health Public Access Author Manuscript, pp. 1-30; published in final edited form as *Annu. Rev. Biochem.*, 2009, vol. 78, pp. 177-204.

Wille, Holger et al., "Natural and synthetic prion structure from X-ray fiber diffraction", *PNAS*, Oct. 6, 2009, vol. 106, No. 40, pp. 16990-16995.

* cited by examiner

*Primary Examiner* — Christopher R. Tate
(74) *Attorney, Agent, or Firm* — Foley & Lardner LLP

(57) ABSTRACT

Methods for the degradation of prion proteins are described. Items that may be contaminated with prions are treated with earthworm-derived extracts to degrade prion proteins and reduce their infectivity in animals. Methods of using an earthworm-derived protein extract for treating foodstuffs and surfaces to inhibit or disable prion infectivity are disclosed. Also disclosed are methods for treating medical instruments, tools used to butcher animals, and laboratory equipment.

17 Claims, 4 Drawing Sheets

A

B

A

B

DEGRADATION OF PRION PROTEIN AND REDUCED PRION INFECTIVITY BY EARTHWORM HOMOGENATES

CROSS-REFERENCE TO RELATED APPLICATIONS

This application claims priority to U.S. Provisional Patent Application No. 61/099,944, filed Sep. 25, 2008, the entire contents of which are hereby incorporated by reference in its entirety.

GOVERNMENT SUPPORT

This invention was made with United States government support awarded by the following agencies: ARMY/MRMC DAMD17-03-1-0369. The United States Government has certain rights in this invention.

TECHNICAL FIELD

The present technology relates generally to the field of biological decontamination. The technology finds particular application in preventing or inhibiting the spread of prion-related diseases.

BACKGROUND

The following description is provided to assist the understanding of the reader. None of the information provided or references cited is admitted to be prior art to the present invention.

Transmissible spongiform encephalopathies (TSE) are untreatable and fatal neurodegenerative diseases that affect a number of mammalian species. Variants of TSE affect humans and many wild and domesticated animals. Examples of TSE are bovine spongiform encephalopathy (BSE) in cattle (also known as "mad cow disease"), scrapie in sheep, chronic wasting disease (CWD) in moose, deer and elk, and Creutzfeldt-Jakob disease (CJD) in humans. (Prusiner, *Brain Pathol*, 8:499-513 (1998).) All these diseases attack the neurological system and are characterized by initially long incubation followed by a short period of neurological symptoms, including dementia, loss of coordination, and eventually death.

The infectious agents that cause and transmit TSE are called prions. Prions are abnormally folded variants ($PrP^{Sc}$) of naturally occurring and normally harmless cellular proteins ($PrP^C$). Prions are not believed to be associated with cells or virus particles, and most evidence shows that prions have no associated nucleic acids or other genetically transmissible material. In humans, the prion protein is encoded by the PRNP gene, which resides on chromosome 20. The protein is most commonly found in neurons, and in lower amounts in other cells such as leukocytes, monocytes, and platelets. (Holada et al., *Lancet* 356:1772 (2000).) When the normal cellular form of the prion protein is misfolded, the prion is able to infect and propagate by converting other normal molecules of the protein into the abnormally folded form. Thus, diseases caused by prions are characterized by accumulation of the misfolded form of the normal cellular prion protein. (Prusiner, *PNAS*, 95:13363-13383 (1998).) The misfolded form is extremely stable and accumulates as plaques in infected tissue, causing cell death and tissue damage that manifests as holes and a spongy appearance. The misfolded disease form of the prion protein is predominantly found in the brain, but has also been detected in the tonsil, spleen, and lymph nodes of infected humans.

Horizontal transmission is implicated in spreading the infectious agent causing scrapie in sheep and chronic wasting disease (CWD) in free-ranging cervids. (Hoinville, *Rev Sci Tech*, 15:827-852 (1996); Miller & Williams, *Nature*, 425:35-36 (2003).) The recent expansion of endemic regions of CWD in North America emphasizes the need to identify transmission routes. Several studies have advanced soil as a contributor to horizontal transmission, suggesting it acts as an environmental reservoir for retaining and facilitating exposure of susceptible animals to the infectious agent. (Johnson et al., *PLoS Pathog*, 2(4) (2006); Johnson et al., *PLoS Pathog*, 3(7) (2007), Seidel et al., *PLoS ONE*, 2(5) (2007).) TSE infectious agents can enter the soil environment from the decomposing carcasses of infected animals as well as from the excreta and saliva shed from infected animals. In addition, prion diseases can be transmitted by certain high-risk tissues, including the brain, spinal cord, cerebral spinal fluids, and the eye. After a surgical procedure on a prion-infected patient, or the butchering of a prion-infected animal, prion-containing residue may remain on the instruments and tools. During the long incubation period of prion-associated diseases, it is extremely difficult to determine if a person or animal is a prion carrier.

TSE infectious agents can survive in the environment for years (Seidel et al., *PLoS ONE*, 2(5) (2007)), subsequently serving as a long-term source of infection. Deer can become infected with CWD when exposed to facilities that previously contained decomposed infected carcasses and/or soil contaminated with excreta from infected animals. (Miller et al., *Emerg Infect Dis*, 10:1003-1006 (2004).) In addition, clay-bound prions are significantly more infectious than unbound $PrP^{Sc}$. (Johnson et al., *PLoS Pathog*, 2(4) (2006); Johnson et al., *PLoS Pathog* 3(7) (2007).)

SUMMARY

The present technology generally relates to biological decontamination, and to aspects of contacting surfaces with a composition to minimize or eliminate contamination with infectious prions. In one aspect, this disclosure provides a method for degrading prions, the method comprising contacting a surface that carries or is suspected to carry prion-infected material with an effective amount of composition comprising an earthworm extract or an active fraction thereof. In one embodiment, the degradation of prions results in a reduction of prion infectivity.

In one embodiment, the composition comprises about 10-30% by weight earthworm extract. In one embodiment, the earthworm extract is an aqueous extract. In one embodiment, the earthworm extract is an earthworm-extracted supernatant. In one embodiment, the earthworm-extracted supernatant is prepared by wet-grinding earthworms and filtering the supernatant. In one embodiment, the earthworm extract is lumbrokinase enriched from a crude earthworm extract. In one embodiment, the earthworm extract has been lyophilized. In one embodiment, the lyophilized earthworm extract is prepared by wet-grinding earthworms, filtering the supernatant, followed by freeze-drying. In one embodiment, the earthworm extract is derived from *Lumbricus rubellus, Eisenia fetida*, or *Lumbricus bimastus*.

In one embodiment, wherein the earthworm extract comprises one or more proteases having at least 70%, at least 80%, at least 90%, at least 95%, or at least 99% sequence identity to an earthworm protease selected from the group consisting of SEQ ID NOs: 1-29. In one embodiment, the earthworm extract comprises one or more proteases selected from the group consisting of SEQ ID NOs: 1-29.

In one embodiment, the active fraction of an earthworm extract is a protease-containing fraction from size exclusion chromatography of an earthworm extract. In another embodiment, the active fraction is a protease-containing fraction from ion exchange chromatography of an earthworm extract. In one embodiment, the active fraction is capable of reducing infectivity of prions by at least 75% compared to a control, as measured by an infectivity assay of a living mammalian subject. In one embodiment, the subject is a hamster or a mouse.

In one embodiment, the pH of the composition is from about 6 to 8. In one embodiment, the contacting step is performed at a temperature of from about 20 to about 50° C.

In one embodiment, the surface is the surface of a medical device. In one embodiment, the surface is the surface of butchering equipment. In one embodiment, the surface is the surface of laboratory equipment used in prion research.

In one embodiment, the step of contacting comprises soaking the surface in the composition. In one embodiment, the soaking has a duration of at least 30 minutes. In one embodiment, the step of contacting comprises spraying or wiping the surface with the composition. In one embodiment, following the treating of the surface, the prion-infected material is unable to infect a live mammal.

In another aspect, this disclosure provides a method for inhibiting infection by an infectious prion, the method comprising adding a composition that degrades prions to an animal foodstuff containing or suspected of containing a prion-infected material, wherein the composition comprises an effective amount of an earthworm extract or an active fraction thereof, and wherein prions in the foodstuff, if present, are degraded.

In another aspect, this disclosure provides a foodstuff that has been treated with a composition that degrades prions, wherein the composition comprises an effective amount of an earthworm extract or an active fraction thereof, and wherein prions in the foodstuff, if present, are degraded.

In another aspect, this disclosure provides a method for identifying an active fraction of an earthworm extract that reduces prion infectivity, comprising the steps of: (a) contacting one or more earthworm extracts or fractions thereof with a prion-containing material; (b) following step (a), contacting the prion-containing material with an animal host; and (c) measuring the level of prion infectivity in the animal host, wherein a reduced level of prion infectivity in the animal host compared to a control sample indicates that the one or more earthworm extracts or fractions thereof are effective in reducing prion infectivity. In one embodiment, the method further comprises the step of comparing levels of prion infectivity from different fractions of earthworm extracts. In one embodiment, the method further comprises the step of comparing levels of prion infectivity from different earthworm extracts.

BRIEF DESCRIPTION OF THE FIGURES

FIG. 1A shows whole worm protein extracts assayed for hamster prion protein from earthworms exposed to infectious brain material in soil. FIG. 1B shows protein extracts from prion-exposed earthworms bisected into anterior and posterior sections and total proteins extracted (a=anterior; p=posterior).

FIG. 2A shows digestion of $PrP^{CWD}$ with dilutions of clarified earthworm protein extracts. FIG. 2B shows digestion of PTA-enriched $PrP^{CWD}$ with dilutions of lumbrokinase.

FIG. 3A shows 1, 2, 4 and 8 day incubations of $PrP^{HY}$ and earthworm protein. FIG. 3B shows dilutions of $PrP^{HY}$ treated for 8 days with earthworm protein extracts.

DETAILED DESCRIPTION

Figure 1:
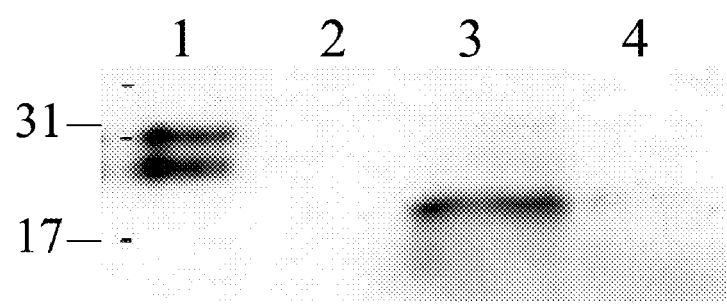
FIG. 1 shows western blots demonstrating the degradation of prion proteins by earthworms.
Figure 1:
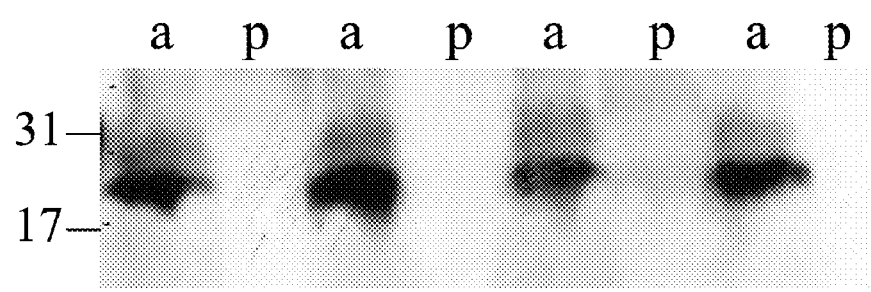

The technology relates to compositions of earthworm-derived extracts or homogenates that degrade prion proteins, methods of using the compositions to decontaminate surfaces, instruments, tools, and foodstuffs, and a foodstuff prepared by applying the methods and compositions. It will be appreciated that the compositions and methods disclosed are amenable for treating of a wide range of items that may be contaminated with prion infected material.

In practicing the present technology, many conventional techniques in molecular biology, protein biochemistry, cell biology, immunology, and microbiology are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y. (1989)); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press (1986)); Perbal, *A Practical Guide to Molecular Cloning*; the series, *Meth. Enzymol.* (Academic Press, Inc. (1984)); *Gene Transfer Vectors for Mammalian Cells*, Miller & Calos, Eds. (Cold Spring Harbor Laboratory, NY (1987)); and *Meth. Enzymol.*, Vols. 154 and 155, Wu & Grossman, and Wu, Eds., respectively. Units, prefixes, and symbols may be denoted in their accepted SI form.

In the description that follows, a number of terms are utilized extensively. Definitions are herein provided to facilitate understanding of the invention. The terms described below are more fully defined by reference to the specification as a whole.

As used herein, the terms "a" and "an" mean "one or more" unless the singular is expressly specified.

As used herein, when referring to a numerical value or other quantity, the term "about" means within plus or minus 10% of the enumerated value unless stated otherwise.

As used herein, the term "activity" describes quantitatively the conversion of a given substrate under defined reaction conditions.

As used herein, "to degrade" or "to digest" refers to the process of breaking down a protein or other macromolecule into simpler components, which causes a decrease in that macromolecule's abundance or activity.

As used herein, "effective amount" of a composition refers to a quantify sufficient to achieve a desired standard of prion removal, degradation, or destruction, or a desired standard of reduced infectivity.

As used herein, "horizontal transmission" refers to the transmission of an infectious agent by a means other than by genetic inheritance from parent to child.

As used herein, "infectivity" refers to the ability of a prion-contaminated substance, item, or surface to cause a prion-associated disease in an individual.

As used herein, the terms "preventing" or "prevention" refer to a reduction in the risk of acquiring a disease or disorder (i.e., causing at least one of the clinical symptoms of the disease not to develop in a patient that may be exposed to the disease but does not yet experience or display symptoms of the disease). In the context of the present technology, prevention includes interfering with the mechanism of transmitting prion-based diseases.

As used herein, the terms "polypeptide," "peptide," and "protein" are used interchangeably to refer to a polymer of amino acid residues. The terms polypeptide, peptide, and protein are also inclusive of modifications including, but not limited to, glycosylation, lipid attachment, sulfation, carboxylation, hydroxylation, ADP-ribosylation, and addition of other complex polysaccharides.

As used herein, the term "protease" means any protein molecule catalyzing the hydrolysis of peptide bonds. It includes naturally-occurring proteolytic enzymes, as well as protease variants. It also comprises any fragment of a proteolytic enzyme, or any molecular complex or fusion protein.

As used herein, the term "$PrP^C$" refers to the native prion protein molecule, which is naturally and widely expressed within the bodies of mammals. Its structure is highly conserved and is not believed to be associated with a disease state.

As used herein, the term "$PrP^{CWD}$" refers to a prion protein isolated from an animal diagnosed as having chronic wasting disease.

As used herein, the term "$PrP^{HY}$" refers to a prion protein purified from a prion-infected hamster.

As used herein, the term "$PrP^{Sc}$" refers to the conformationally altered form of the $PrP^C$ molecule that is believed to be associated with TSE and prion diseases. $PrP^{Sc}$ has the same amino acid sequence as normal, cellular $PrP^C$, but has an altered folded conformation in which some of the α-helix is converted to β-pleated sheet.

As used herein, the term "PrP" refers to a prion protein in general.

As used herein, the term "$PrP^{TSE}$" refers to a PrP that causes a transmissible spongiform encephalopathy.

As used herein, the term "sequence identity" means that two polypeptide sequences are identical (i.e., on a amino acid-by-amino acid basis) over the window of comparison. The term "percentage of sequence identity" is calculated by comparing two optimally aligned sequences over the window of comparison, determining the number of positions at which the identical amino acid occurs in both sequences to yield the number of matched positions, dividing the number of matched positions by the total number of positions in the window of comparison (i.e., the window size), and multiplying the result by 100 to yield the percentage of sequence identity.

As used herein, "transmissible spongiform encephalopathy" (TSE) refers to a group of inevitably fatal progressive disease conditions that affect the brain and nervous system of animals, causing the deterioration of mental and physical abilities and causing tiny holes to appear in the cortex causing it to appear like a sponge. TSE diseases include, but are not limited to, classic Creutzfeldt-Jakob disease, variant Creutzfeldt-Jakob disease, kuru, fatal familial insomnia, GSS, scrapie, BSE, CWD, and other TSEs, including rare TSEs of captive and experimental animals. These conditions form a spectrum of diseases with overlapping signs and symptoms.

Overview

Described herein are compositions and methods for degrading prions to minimize or eliminate their infectivity. The extreme stability of the protein causes prions to be resistant both to degradation by the infected host and to denaturation by many physical and chemical means outside the host. In addition, prions are resistant to routine methods of decontamination and sterilization. Infectious particles possessing nucleic acid (DNA or RNA) are dependent upon it to direct their continued replication. Prions, however, are infectious by their effect on normal versions of the protein. Therefore, sterilizing prions involves the denaturation or degradation of the protein to a state where the molecule is no longer able to induce the abnormal folding of normal proteins. Glutaraldehyde, formaldehyde, ethylene oxide, liquid hydrogen peroxide, most phenolics, alcohols, dry heat, boiling, freezing, ultraviolet radiation, ionizing radiation, and microwave radiation have generally been reported to be ineffective. More extreme conditions are required to inactivate prions—for example, a one-hour exposure to a NaOCl solution containing 20,000 ppm of $Cl_2$ or autoclaving in 1 N NaOH are methods that are recommended for inactivating prions.

Common earthworms have the capacity to ingest soil particles and, in the process of digestion, degrade prion proteins and decrease their associated infectivity. The earthworm species *Lumbricus rubellus* and *Eisenia fotida* originated as exotic species introduced from Europe, but now have successfully competed with native species and range from the northeast and south-central United States to the Western Great Lakes and Pacific coast. (Reynolds et al., *Earthworm Ecology and Biogeography* in North America, Hendrix, ed. CRC Press, Inc., Florida, USA (1995) 1-28; Hendrix & Bohlen, *Bioscience*, 52:801-811 (2002).) Extracts and active fractions from these and other earthworm species are useful in the methods described below.

Preparation of Compositions

In one aspect, the compositions disclosed herein contain an earthworm homogenate, an earthworm extract, an active fraction of an earthworm extract, and/or one or more purified proteases found in earthworm extracts. The extracts, fractions, and purified proteases can be prepared by a variety of methods. For example, an earthworm homogenate can be produced by mechanical means such as grinding, wet-grinding, pulverizing, blending, smashing, or mixing whole earthworms into an homogenous mixture. Chemical processes might also be suitable. One method of producing an earthworm homogenate is to quick freeze worms in liquid nitrogen, pulverize the frozen worms with a mortar and pestle, and then resuspend the resulting powdered earthworm tissue in a suitable buffer, for example, phosphate-buffered saline. In one embodiment, a useful resuspension contains from about 1-75%, from about 5-60%, from about 5-50%, or from about 10-30% by weight of earthworm tissue. The resuspension may be filtered (e.g., using diatomaceous silica), centrifuged, or treated in any other suitable manner known to those of the art to remove insoluble or other particulate matter that may be present in the preparation. The preparation may be stored as a liquid resuspension or as a frozen solid.

Those of skill in the art are able to select and prepare a buffer suitable for resuspending the homogenate. Some components of buffers are salts, chelating agents to inhibit enzymatic degradation of active components, and preservatives to inhibit contamination by microbial growth. Another important parameter of a buffer is its pH. One buffer that is useful for preparing an earthworm homogenate contains about 130 mM NaCl, about 3 mM KCl, about 10 mM $NaHPO_4$, and about 1.8 mM $KH_2PO_4$. Many biologically-derived products typically function at a pH of about 7. Thus, a suitable pH for such a buffer is from about 6 to about 8.

In one embodiment, the earthworm extract or homogenate may be lyophilized and stored as a powder. Lyophilization is a dehydration process typically used to preserve a perishable material or to make a material more convenient to transport or store. The process involves freezing the material under low pressure and using a small amount of heat to remove water from the material. Other names for the process are freeze drying and cryodesiccation. Cryoprotectants or lyoprotectants may be added to provide additional protection to the lyophilized preparation. Some lyoprotectants are certain sugars, such as the natural substances sucrose and trehalose, and polyalcohols. The preparation may be lyophilized before or after resuspension in a suitable buffer. Furthermore, the lyophilized preparation may then be used in the disclosed methods either directly as a powder or after reconstitution by adding water or another appropriate buffer or solvent. For example, the lyophilized powder may be added to an animal feed or other foodstuff to inhibit the infectivity of any prions that may be present. Alternatively, a liquid preparation may be more suitable for treatment of a surface.

In one embodiment, the protein extract is derived from earthworms categorized in the class or subclass Oligochaeta, which are members of the phylum Annelida. In accordance with the methods disclosed, one of skill in the art could determine the effectiveness of a preparation derived from any particular variety of earthworm. In particular, members of the genera *Lumbricus* (red worms) and *Eisenia* (tiger worms) are useful for preparing an effective composition. Moreover, in one embodiment of the technology, the earthworm protein homogenate is derived from the earthworm species *Lumbricus rubellus* or *Eisenia fetida*.

In one embodiment, a composition useful in the present methods is lumbrokinase. Enzymes extracted from earthworms are collectively called lumbrokinase (LK). (Nakajima et al. *Biosci Biotechnol Biochem*, 63:2031-2033 (1993); Cho et al., *J Biochem Mol Biol*, 37:199-205 (2004).) Lumbrokinase is commercially available as a semi-purified earthworm extract from *L. rubellus* containing a complex of earthworm fibrinolytic enzymes. One method of preparing LK is disclosed in publication number JP 2005230013. Briefly, an earthworm homogenate slurry is filtered, centrifuged, and passed through an anion exchange or affinity chromatography column, followed by concentrating, desalting, and lyophilizing the eluant. Alternative methods of production using chromatography are described in JP 2007039404, and additional purification and preparation steps are described in publication number CN 1587398.

In some embodiments, lumbrokinase is used as an agent to degrade PrP or reduce the infectivity of PrP. LK degrades abnormally folded proteins, such as the infective prion protein $PrP^{Sc}$, with an effectiveness similar to earthworm homogenates generally. In another embodiment, the earthworm homogenate is an active fraction of lumbrokinase. Active fractions of LK (e.g., LrP II and LrP III), and similar preparations from *E. fetida* may also be used in the present methods.

Active fractions of an earthworm extract can include, but are not limited to, proteins, carbohydrates, or combinations thereof (e.g., glycoproteins) that, alone or in combination with other components, can reduce prion infectivity (as measured using the assays described herein). Numerous separation procedures can be employed to further purify desired components or remove unwanted or contaminating components, including decanting, filtration, sedimentation, centrifugation, heating, adsorption, precipitation, chromatography, or ion exchange. The resulting active fraction can be subsequently concentrated by evaporation, vaporization, lyophilization or vacuum drying.

One method includes obtaining an extract of earthworm material and size-fractionating the extract, e.g., through a size exclusion column. Another method includes obtaining an extract of earthworm material and fractionating the extract using ion exchange chromatography. Chromatography may be performed in column or batch mode. In column chromatography, a sample is loaded onto the column and eluted with successively higher concentrations of a solvent. Other purification methods which may be used in addition to reverse phase chromatography include low pressure column chromatography, batch chromatography, precipitation, specific adsorbent chromatography, gel filtration, HPLC and combinations of these methods. Using these or similar methods of fractionating a earthworm extract, one or more active fractions capable of degrading prions and/or reducing prion infectivity may be obtained.

In one embodiment, the composition comprises one or more earthworm proteases. In some embodiments, the one or more earthworm proteases are selected from the group consisting of SEQ ID NOs: 1-29, shown in Table 1.

TABLE 1

Exemplary Earthworm Proteases

| Name | Species | GenBank Accession No. | SEQ ID NO: |
|---|---|---|---|
| Fibrinolytic enzyme | Lumbricus rubellus | BAB40767 | 1 |
| Fibrinolytic enzyme | Lumbricus rubellus | BAB40768 | 2 |
| Fibrinolytic protease 0 | Eisenia fetida | ABG68022 | 3 |
| Fibrinolytic protease 1 | Eisenia fetida | ABD76397 | 4 |
| Fibrinolytic protease 2 | Eisenia fetida | ABG68023 | 5 |
| Fibrinolytic protease P-III-1 | Eisenia fetida | ABB19359 | 6 |
| Fibrinolytic enzyme | Lumbricus bimastus | AAD05563 | 7 |
| Lumbrokinase | Lumbricus bimastus | AAL28118 | 8 |
| Lumbrokinase | Lumbricus rubellus | AAN58692 | 9 |
| Lumbrokinase | Lumbricus bimastus | AAN78282 | 10 |
| Lumbrokinase | Lumbricus bimastus | AAP04532 | 11 |
| Lumbrokinase | Eisenia fetida | AAT74899 | 12 |
| Lumbrokinase | Eisenia fetida | AAT74900 | 13 |
| Lumbrokinase | Eisenia fetida | AAW27919 | 14 |
| Lumbrokinase | Eisenia fetida | ABQ23217 | 15 |
| Lumbrokinase | Eisenia fetida | ABW04903 | 16 |
| Lumbrokinase | Eisenia fetida | ABW04904 | 17 |
| Lumbrokinase | Eisenia fetida | ABW04905 | 18 |
| Lumbrokinase | Eisenia fetida | ABW04906 | 19 |
| Lumbrokinase-1T4 | Lumbricus rubellus | AAA96502 | 20 |
| Lumbrokinase-3 | Eisenia fetida | AAR13224 | 21 |
| Lumbrokinase-3(1) | Lumbricus rubellus | AAA96503 | 22 |
| Lumbrokianse-3T2 | Lumbricus rubellus | AAQ13828 | 23 |
| Lumbrokinase-4 | Eisenia fetida | AAR13225 | 24 |
| Lumbrokinase-5 | Eisenia fetida | AAR13226 | 25 |
| Lumbrokinase-7T1 | Lumbricus rubellus | AAQ13829 | 26 |
| Lumbrokinase-7T2 | Lumbricus rubellus | AAQ13830 | 27 |
| Lumbrokinase-Da2 | Lumbricus rubellus | AAQ13831 | 28 |
| Lumbrokinase-P2(2) | Lumbricus rubellus | AAQ15052 | 29 |

In some embodiments, the one or more earthworm proteases will possess a certain amount of sequence identity to the proteases of SEQ ID NOs: 1-29. For instance, earthworm proteases useful in the claimed methods includes derivatives of the amino acid sequences of SEQ ID NOs: 1-29 having one or more substitutions, additions and/or deletions, including one or more non-naturally occurring amino acids. Preferably, derivatives exhibit at least about 50% identity to any wild type or reference sequence, preferably at least about 70% identity, more preferably at least about 75%, 80%, 85%, 90%, 91%, 92%, 93%, 94%, 95%, 96%, 97%, 98%, 99% or 100% sequence identity to any wild type or reference sequence described herein. Sequence (or percent) identity can be determined according to methods known in the art. Derivatives can also include post-translational modifications of the polypeptide, for example, glycosylation, acetylation, phosphorylation, and the like.

Peptide derivatives can also include any of these modifications so long as the polypeptide maintains the desired activity. These modifications may be deliberate, as through site-directed mutagenesis, or may be accidental, such as through mutations of hosts that produce the proteins or errors due to PCR amplification. Furthermore, modifications may be made that have increase affinity and/or specificity for prion proteins. Polypeptides described herein can be made recombinantly, synthetically, purified from natural sources, or in tissue culture.

Methods of Degrading Prions and Reducing Prion Infectivity

In one aspect of the present technology, the composition is effective in reducing prion infectivity. In general, infectivity refers to the ability of a pathogen to establish an infection in an individual. Thus, infectivity refers to the relative capability of a prion-contaminated object, substance, or surface to transmit one or more prions to, or cause a prion-associated disease (i.e., a TSE), in an animal; thus, reduced infectivity is marked by a decreased ability to transmit a prion or cause a prion disease. A reduction in infectivity can be expressed in relative terms as a ratio, fraction, or percentage describing the infectivity after a treatment relative to the infectivity prior to the treatment. Thus, reduced infectivity can be expressed by saying the infectivity is about 99%, 95%, 90%, 80%, 70%, 60%, 50%, 40%, 30%, 20%, 10%, 5%, 1%, 0.1%, 0.01% or 0.001% of the untreated control.

Several measures can be used to demonstrate reduced infectivity. For example, two similar prion-free, healthy populations or test subjects are exposed to a prion-contaminated object or substance that either has or has not been treated with an earthworm homogenate under certain conditions. A reduced infectivity is indicated by disease symptoms not manifesting or manifesting after a longer interval of time in the population or subject that was exposed to the object or substance that was treated. In some embodiments, the present methods can be used to degrade prions such that the incubation time for the disease is substantially lengthened and/or infectivity is reduced. In particular, treatment with earthworm homogenate or an active fraction thereof may reduce prion infectivity to less than about 0.01% (one-ten thousandth) of the value observed from an untreated control.

In addition, a reduced incidence (rate of occurrence of initial infections) of prion-associated disease in a controlled population indicates a reduced infectivity. When two similar prion-free, healthy populations are exposed to a prion-contaminated object or substance that either has or has not been treated by a method described herein, a reduced infectivity is indicated by observing a smaller infected subset of subjects among the population that was exposed to the object or substance that was treated.

In an illustrative embodiment, the activity of one or more earthworm extracts or active fractions thereof may be measured using a live animal assay. For example, purified hamster prions ($PrP^{HY}$) are incubated in the presence of earthworm extract or an active fraction thereof. The samples are then intracerebrally inoculated into weanling Syrian hamsters. A dilution series of $PrP^{HY}$ may also be inoculated as a control. Hamsters are monitored on a regular basis for the onset of clinical symptoms. Brains from clinically positive hamsters and uninfected controls are analyzed for protease-resistant PrP by immunoblotting.

Methods of Decontaminating Surfaces

Aspects of the present technology relate to contacting an object, surface, or substance with a composition containing an earthworm homogenate, an active fraction thereof, or one or more purified earthworm proteases to degrade prions that may be present. In one embodiment of the methods disclosed, the contacting is performed by soaking the surface in the composition. Other methods of contacting the surface with the composition can also be used such as immersing or dunking the surface in the composition, or coating, spraying, wiping, layering, or wetting the surface with the composition. The length of time of contacting the surface with the composition can be varied. In some embodiments, the contact is maintained by soaking for up to 30 minutes. In other embodiments, the contact is maintained by soaking for at least 30 minutes. In yet other embodiments, the contact is maintained until an effective or desired reduction in infectivity has been achieved.

Many types of surfaces may become contaminated with prions during their use. Any tool or instrument that is used to cut, slice, chop, or otherwise touch in any way the tissues or fluids of an animal, including human tissue or fluid, could become contaminated. Examples of items that could be exposed to prions and would need decontamination are medical devices used in surgical procedures, such as scalpels, scissors, endoscopes, forceps, catheters, retractors, clamps, spatulas, and the like, equipment used for butchering an animal, such as a knife, and laboratory equipment that is used in prion research such as homogenizers, tubes, spatulas, and the like. Prions can also be present in animal excreta, saliva, mucus, blood, lymph, tears, and other fluids originating from a live infected animal, and these substances can attach to and contaminate a surface. Surfaces that can become contaminated are tables and other fixtures that are used to support a patient or animal for surgery, butchering, or other procedures, i.e., medical equipment, surgical implements, pharmaceutical equipment, mortuary equipment, meat processing equipment, food handling equipment, cookware, and the like. Contamination can occur on surfaces present in professional environments such as operating rooms, hospitals, veterinary clinics, ambulances, and the like, in commercial environments such as those involved with food processing, fur production, animal husbandry, and the like, and in home environments such as a garage, barn, or kitchen, for instance, where a person stores or butchers a deer or other game.

In addition, other substances and surfaces can become contaminated with prions. For instance, foodstuffs, feed, and animal chow can contain prions, and this food can subsequently infect animals and humans that ingest the prion-contaminated food. For example, the "mad cow disease" (BSE) scare and the incidence of a new variant of human CJD (vCJD) are considered to be a consequence of dietary exposure to scrapie sheep carcasses rendered for animal feed in the case of BSE (Brown et al., *JAMA* 278:1008-1011 (1997)), and to beef from cattle affected with BSE in the case of vCJD. (Bruce et al., *Nature* 389:498-501 (1997).) There is also evidence of cross-species infectivity of prions. In the case of BSE and vCJD, epidemiological data places the majority of vCJD cases in the UK where the overwhelming majority of BSE cases have been reported. This link is supported by evidence obtained from studies in macaques and mice demonstrating cross-species infectivity of prions, and additional studies showing transmission of mouse-adapted strains to hamsters, transmission of human strains to ferrets and goats after passage through primates and cats, and transmission of a bovine strain to hamsters after passage through mice. Some measures have been introduced to limit human exposure to prions—ruminant protein feed has been banned in the US and UK to reduce the number of BSE cases, and other measures have been taken to prevent potentially infected meat from entering the human food chain. Also, the FDA and CBER have declined to accept blood from donors who stayed in the UK for more than 6 months during 1980-1996.

Despite these precautions and because modes of prion transmission are not well understood, many potential means of food contamination are still possible. For instance, animal feed can become contaminated by contacting prion-containing soil. A human could then become infected by ingesting meat from an animal previously infected by prion-contaminated feed. Foodstuffs can become contaminated by coming into contact with equipment, implements, tools, or machines that had previously been used to prepare prion-infected matter. Thus, the present technology includes methods for adding an effective amount of an earthworm homogenate composition to an animal foodstuff to degrade any prions that may be present.

The activities of biologically-derived compositions can vary with physical conditions. Temperature and pH are two common parameters that may influence the activity of such a composition. Most biological systems maintain a neutral pH of 7 or a near-neutral pH, and thus compositions prepared from a biological system often are used at a neutral or near-neutral pH. In one embodiment of the methods described, the pH of the composition is from about 6 to 8. The temperature of 37° C. is human body temperature, and is often used with biological preparations. Most pieces of laboratory or medical equipment can maintain this temperature. In one embodiment of the method, the contacting step is performed at a temperature of 37° C. In other embodiments, the contacting step is performed at a temperature of from about 20 to about 50° C. Earthworms live and grow in the soil, where environmental conditions may vary over a wide range of temperatures. Thus, in yet other embodiments of the methods disclosed, the contacting step is performed at a temperature of from about 0-30° C., from about 10-40° C., or from about 30-60° C.

EXAMPLES

The present invention is further illustrated by the following examples, which should not be construed as limiting in any way.

Materials and Methods

Earthworms. The earthworms used in this study were commercially raised, common garden earthworms (*Lumbricus rubellus* and *Eisenia fetida*). Earthworm homogenates were prepared by quick-freezing worms in liquid nitrogen, then pulverizing the sample using a mortar and pestle. The powdered tissue was resuspended in buffered saline (PBS, 130 mM NaCl, 3 mM KCl, 10 mM $Na_2HPO_4$ and 1.8 mM $KH_2PO_4$, pH 7.4) to 30% (w/v). Earthworm homogenates were centrifuged for 5 min at 3000 rpm to remove particulates. Clarified extracts were transferred to clean tubes and stored at −20° C. For anterior and posterior extracts, earthworms were bisected and each half processed as above.

Lumbrokinase. Lumbrokinase (LK), in capsule form, was purchased from the Allergy Research Group (Alameda, Calif.). The enzyme powder was removed from the gelatin capsule and resuspended in $ddH_2O$ to make a 400 mg/ml (w/v) stock solution. The LK suspension was centrifuged at 3000 rpm for 5 min and the clarified supernatant was collected.

Purified TSE agents. Brains from deer affected with CWD were homogenized with PBS in a Dounce homogenizer to 20% (w/v). For other experiments, brains from Syrian hamsters clinically affected with the Hyper strain of hamster-adapted transmissible mink encephalopathy agent were homogenized in PBS to 10% (w/v). Enriched $PrP^{TSE}$ was prepared using a variation of the phosphotungstic acid (PTA) precipitation. Equal volumes of brain homogenate and sarkosine were mixed with $CaCl_2$ and DNAse (final concentration: 2% sarkosine, 10 mM $CaCl_2$, and 100 µg/ml DNAse) and incubated overnight at 37° C. on a platform rocker. After centrifuging 3000 rpm for 5 min, the supernatant was transferred to a clean tube. PTA (4% in 170 mM $MgCl_2$) was added to the supernatant (final concentration 0.2%) and incubated on a platform rocker overnight at 37° C. The enriched preparations were then centrifuged at 14,000 rpm for 30 min, the resulting pellet resuspended in PBS (1/10 starting volume) by sonication and finally incubated with proteinase K (50 µg/ml) for 30 min at 37° C.

Earthworm/TSE environment. Earthworms (n=6 to 10) were placed in a small container with 50 g of commercial top-soil (soil, peat moss, humus, and sand). Hamster brain tissue (~1 g) from a clinically affected hamster (Hyper strain) was added to the soil and the container was covered for 1-10 days at room temperature. At specified time intervals, earthworms were removed from this environment, rinsed in $ddH_2O$ and homogenized in PBS. A duplicate container of earthworms with no infectious agent served as a control.

Prion Degradation. Earthworm homogenates (30% w/v) and dilutions of the clarified homogenate (30%, 10%, 5%, 1% in PBS) were spiked with a constant volume of PTA-enriched $PrP^{Sc}$ ($PrP^{CWD}$ or $PrP^{HY}$), vortexed, and incubated at 37° C. Diluted LK solutions (200, 100, 50, 25, and 4 mg/ml in PBS) were incubated at 37° C. with matching amounts of PTA-enriched $PrP^{Sc}$. Equivalent amounts of earthworm homogenates and LK without added $PrP^{Sc}$, as well as $PrP^{Sc}$ alone, were included as controls. Samples were incubated 0-8 days.

Samples were prepared for western blot analysis by boiling in SDS-PAGE sample buffer (100 mM Tris (pH 8.0), 10% SDS, 7.5 mM EDTA, 100 mM dithiothreitol, and 30% glycerol) for 10 minutes. The samples were separated on 4-20% precast gels (BioRad, Hercules, Calif.), proteins were transferred to polyvinyl difluoride membranes and probed with mAbs 3F4 (hamster) or 6H4 (deer). Detection was achieved using an HRP-conjugated goat anti-mouse immunoglobulin G (IgG) (BioRad) and visualized with SuperSignal Chemiluminescence (Pierce, Rockford, Ill.).

Animal bioassay. PTA-purified hamster agent ($PrP^{HY}$) was incubated in the presence of earthworm proteins and LK. The samples were diluted in PBS (pH 7.4), and 30 µl were intracerebrally inoculated into male, weanling Syrian hamsters (Harlan, Indianapolis, Ind.). A dilution series of PTA-enriched $PrP^{HY}$ was also prepared and similarly inoculated. In addition, animals were inoculated with earthworm homogenate or LK (no infectious agent) as controls. Hamsters were monitored on a regular basis for the onset of clinical symptoms. Brains from clinically positive hamsters and uninfected controls were analyzed for protease-resistant PrP by immunoblotting.

Example 1

Earthworm Digestion of Infectious Agent in Soil

To examine the impact of earthworm digestion of infectious agent, earthworms were removed from the prion infected soil, rinsed in water, and homogenized. Protein extracts were prepared and examined for the presence of $PrP^{Sc}$ by western blot analysis. The detected prion protein migrated faster (~20 KDa) than the brain homogenate control in the SDS-PAGE gel (FIG. 1A). These results suggested that partial degradation of the prion protein occurred within the earthworm. To examine the movement of prion protein through the digestive tract of these earthworms, we bisected individual worms and assayed anterior and posterior sections for the presence of PrP$^{Sc}$. Detectable levels of prion protein in these samples were observed only in the anterior sections (FIG. 1B) with a slight size shift (<31 KDa), suggesting abnormal protein is undergoing degradation prior to entering the earthworm's hindgut. Prion protein was not identified in the posterior sections suggesting complete digestion of detectable prion in the digestive tract of the earthworm. Accordingly, earthworms can ingest infectious tissue, and prion proteins present within that tissue are subsequently digested in the earthworm digestive tract. Lanes in Panel A are as follows: Lane 1: 5% brain homogenate; Lane 2: earthworm in absence of infectious material; Lanes 3 and 4: earthworm homogenate. In Panel B, each pair of lanes shows the prion protein detected in anterior (a) and posterior (p) sections from 4 individual worms.

Example 2

Figure 2:
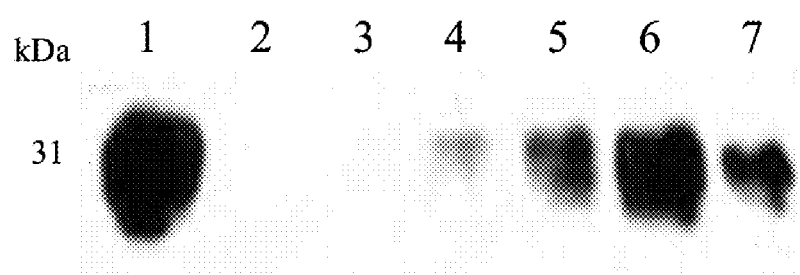
FIG. 2 shows western blots demonstrating in vitro degradation of prion proteins isolated from CWD infected deer by earthworm protein extracts and lumbrokinase.
Figure 2:
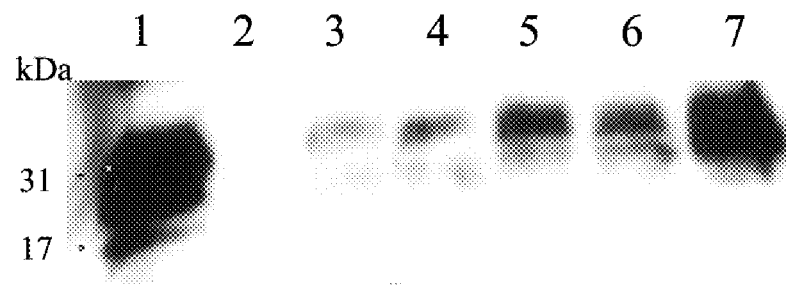

Digestion of CWD Infectious Agent by Earthworm Protein Extracts and Lumbrokinase In Vitro In vitro analyses using PTA-enriched CWD agent incubated with earthworm protein extracts were performed. In these experiments, PTA-PrP$^{CWD}$ was incubated with clarified earthworm protein extracts at 37° C. for set times (t=0, 2, 4, or 8 days) and then immunoblot-tested for prion protein levels. Prion protein immunoreactivity was observed only with the t=0 day sample. For subsequent studies, the digestion times were decreased and dilutions of the earthworm extracts were used. After incubation at 37° C. for 16 h, no prion signal was detected when 30% earthworm protein extract was used, and a weakened signal was seen with a 10% earthworm extract (FIG. 2A). The signal from the control CWD starting agent diluted 1:50 (lane 7) matches the intensity of the 5% earthworm protein dilution sample. The above experiment was repeated with anterior and posterior clarified earthworm protein extract. Anterior derived extract reduced PrP$^{CWD}$ signal similar to the whole worm extract, while protein extract prepared from posterior sections had little effect on the PrP$^{CWD}$. The lanes in Panel A are as follows: Lane 1: PrP$^{CWD}$; Lane 2: worm extract, Lanes 3-6: 30%, 10%, 5%, 1%, respectively, worm extract with CWD agent. Migration of molecular weight markers (KDa) is provided to the left.

Lumbrokinase (LK) is a commercially available, semi-purified earthworm extract containing a complex of earthworm enzymes from *L. rubellus*. The ability of LK to degrade purified prion protein from CWD-infected deer (PrP$^{CWD}$) was assessed. The results are shown in FIG. 2B. The lanes in Panel B are as follows: Lane 1: PrP$^{CWD}$; Lane 2: lumbrokinase, no PrP$^{CWD}$; Lanes 3-7: 200, 100, 50, 25, 4 mg/ml lumbrokinase, respectively. Incubation of LK resulted in loss of PrP$^{CWD}$ signal with the highest enzyme concentrations tested (200 and 100 mg/ml; FIG. 2B). Both earthworm homogenate and LK can digest prions isolated from a deer infected with CWD. Accordingly, earthworm homogenate and LK are effective in methods to degrade or digest prion proteins.

Example 3

Figure 3:
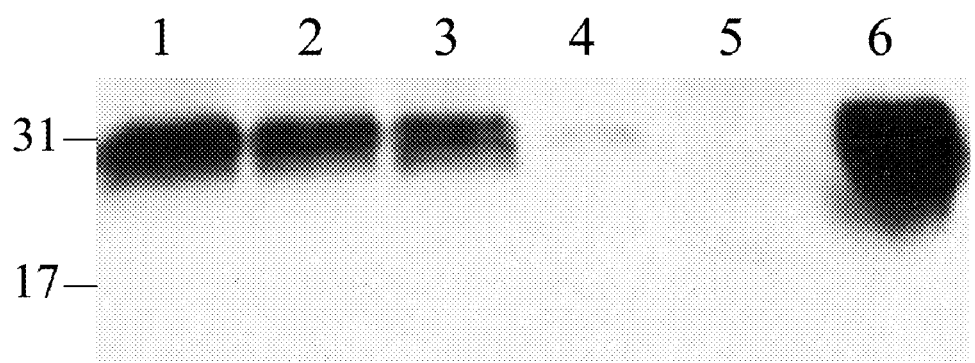
FIG. 3 is a western blot demonstrating in vitro degradation of prion proteins isolated from a hamster model by earthworm protein extracts and lumbrokinase.
Figure 3:
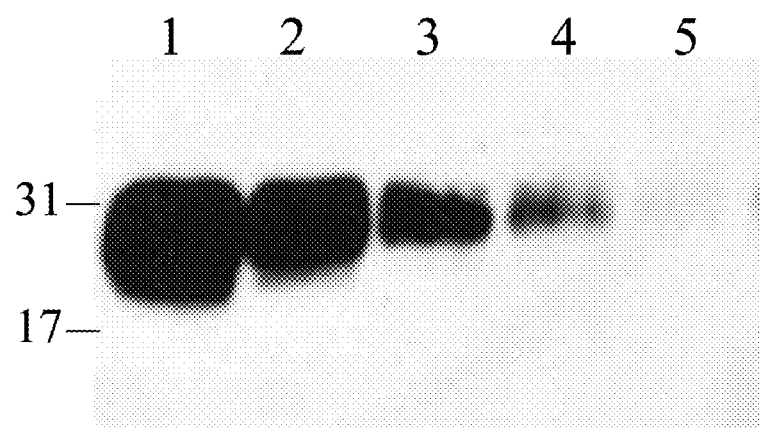
Figure 4:
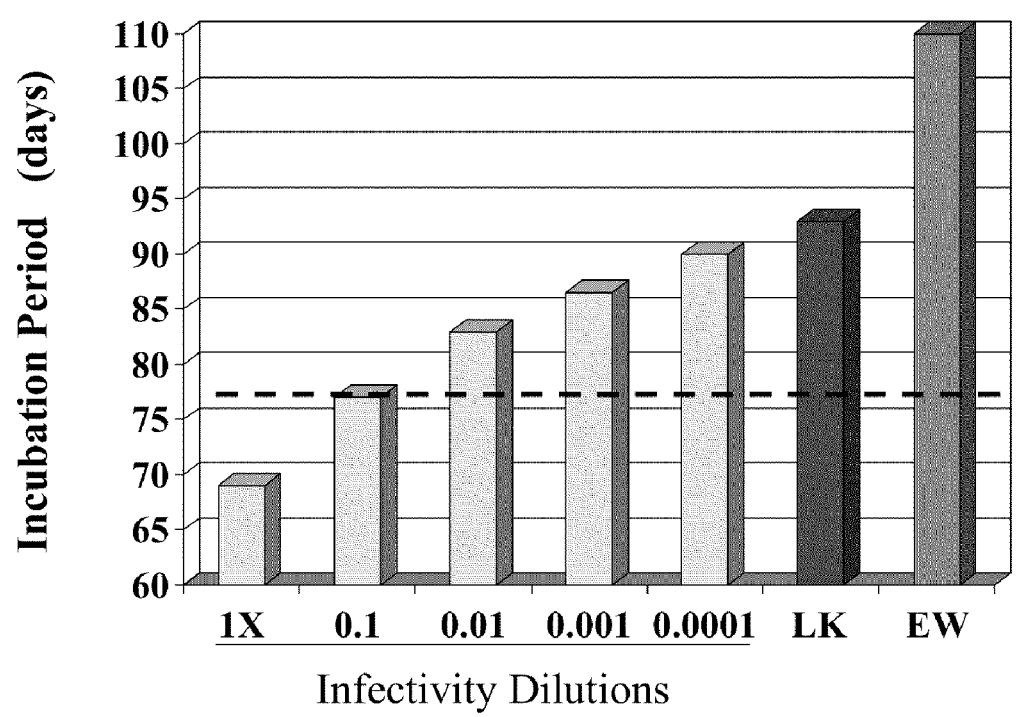
FIG. 4 is a bar graph showing the reduced in vivo infectivity of prion protein that was previously treated in vitro by lumbrokinase or earthworm protein homogenate.

Digestion of Hamster Prion Infectious Agent by Earthworm Protein Extracts and Lumbrokinase In Vitro The ability of earthworm homogenates and LK to degrade prion protein isolated from a hamster-adapted prion model was examined in vitro. Purified hamster prions (PrP$^{HY}$) were incubated in the presence of earthworm protein extracts and (in separate experiments) LK. Similar to purified deer (CWD) prions, both the earthworm extract and the LK degraded PrP$^{HY}$ (FIG. 3). The lanes in Panel A are as follows: Lanes 1-4: 1, 2, 4 and 8 day incubations of PrP$^{HY}$ and earthworm protein, respectively. Lane 5: earthworm extract; Lane 6: PrP$^{HY}$. The lanes in Panel B are as follows: Lanes 1-5: 1:10; 1:20; 1:40; 1:100 and 1:200 (respectively). Migration of molecular weight markers (KDa) is provided to the left. The results show that a considerable decline in prion protein signal was detected after eight days (lane 6). After 8 days of digestion, the amount of PrP$^{HY}$ detected was reduced to approximately one-one hundredth (~0.01) of the untreated sample (comparing lanes 3 & 4, panel A with lanes 4&5, panel B). Thus, in a similar manner to that demonstrated by Example 2, earthworm homogenate and LK can digest prions isolated from a hamster model of prion disease. Accordingly, earthworm homogenate and LK are useful in methods to degrade or digest prion proteins.

Example 4

In Vivo Activity of Infectious Agent after In Vitro Degradation

Animal bioassays were performed to determine if in vitro degradation of prion protein affected infectivity. Increased incubation periods were observed with both the LK and earthworm homogenate-digested prion samples. Compared to control samples (infectious agent only), which had incubation period of 77 days, incubation of infectious agent with LK extended the incubation period to 93 days, while digestion of agent with total earthworm proteins extended incubation period to 110 days. Dilution of infectivity controls indicates that both the LK and earthworm homogenate digestions resulted in a greater than 3 log reduction in infectivity. Accordingly, earthworm homogenate and LK are effective in methods to decrease the infectivity of prion proteins.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 units refers to groups having 1, 2, or 3 units.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method for degrading infectious prion proteins or reducing prion infectivity, the method comprising contacting a surface that carries or is suspected to carry prion-infected material with an effective amount of a composition comprising a whole earthworm tissue homogenate or an active fraction thereof, wherein the composition comprises one or more earthworm tissue-derived prion-degrading enzymes selected from the group consisting of a fibrinolytic enzyme, a fibrinolytic protease, and a lumbrokinase, wherein the active fraction does not consist solely of earthworm digestive tract luminal contents, and wherein the active fraction does not consist solely of lumbrokinase.

2. The method of claim 1, wherein the degradation of prions results in a reduction of prion infectivity.

3. The method of claim 1, wherein the composition comprises about 10-30% by weight of the earthworm tissue homogenate or active fraction thereof.

4. The method of claim 1, wherein the active fraction is an earthworm tissue homogenate supernatant.

5. The method of claim 4, wherein the supernatant is prepared by wet-grinding earthworms and filtering the homogenate.

6. The method of claim 1, wherein the earthworm tissue homogenate or active fraction thereof has been lyophilized.

7. The method of claim 6, wherein the preparation of the lyophilized earthworm tissue homogenate or active fraction thereof comprises wet-grinding earthworms and freeze-drying the tissue homogenate or active fraction thereof.

8. The method of claim 1, wherein the earthworm tissue homogenate or active fraction thereof comprises lumbrokinase.

9. The method of claim 1, wherein the earthworm tissue homogenate or active fraction thereof is derived from an earthworm selected from the group consisting of: *Lumbricus rubellus*, *Eisenia fetida*, and *Lumbricus bimastus*.

10. The method of claim 1, wherein the one or more enzymes has at least 95% sequence identity to an earthworm protease selected from the group consisting of SEQ ID NOs: 1-29.

11. The method of claim 1, wherein the earthworm tissue homogenate or active fraction thereof has been subjected to size exclusion chromatography.

12. The method of claim 1, wherein the earthworm tissue homogenate or active fraction thereof has been subjected to ion exchange chromatography.

13. The method of claim 1, wherein the surface is selected from the group consisting of: a medical device, butchering equipment, and laboratory equipment.

14. The method of claim 1, wherein the step of contacting comprises soaking the surface in the composition.

15. The method of claim 1, wherein the step of contacting comprises spraying or wiping the surface with the composition.

16. The method of claim 1, wherein following the treating of the surface, the prion-infected material is unable to infect a live mammal.

17. A method for inhibiting infection by an infectious prion, the method comprising adding a composition that degrades prions to an animal foodstuff containing or suspected of containing a prion-infected material, wherein the composition comprises an effective amount of a whole earthworm tissue homogenate or an active fraction thereof, wherein the composition comprises one or more earthworm-derived prion-degrading enzymes selected from the group consisting of a fibrinolytic enzyme, a fibrinolytic protease, and a lumbrokinase, wherein prions in the foodstuff, if present, are degraded, wherein the active fraction does not consist solely of earthworm digestive tract luminal contents, and wherein the active fraction does not consist solely of lumbrokinase.

\* \* \* \* \*

```
                           SEQUENCE LISTING

<160> NUMBER OF SEQ ID NOS: 29

<210> SEQ ID NO 1
<211> LENGTH: 245
<212> TYPE: PRT
<213> ORGANISM: Lumbricus rubellus

<400> SEQUENCE: 1

Met Glu Leu Pro Pro Gly Lys Ile Val Gly Ile Glu Ala Arg Pro
1               5                   10                  15

Tyr Glu Phe Pro Trp Gln Val Ser Val Arg Arg Lys Ser Ser Asp Ser
                20                  25                  30

His Phe Cys Gly Gly Ser Ile Ile Asn Asp Arg Trp Val Val Cys Ala
            35                  40                  45

Ala His Cys Met Gln Gly Glu Ser Pro Ala Leu Val Ser Leu Val Val
    50                  55                  60

Gly Glu His Asp Ser Ser Ala Ala Ser Thr Val Arg Gln Thr His Asp
65                  70                  75                  80

Val Asp Ser Ile Phe Val Asn Glu Asn Tyr Asp Pro Arg Thr Leu Glu
                85                  90                  95

Asn Asp Val Ser Val Ile Lys Thr Ala Ile Ala Ile Thr Phe Asp Ile
                100                 105                 110

Asn Val Gly Pro Ile Cys Ala Pro Asp Pro Ala Asn Asp Tyr Val Tyr
            115                 120                 125

Arg Lys Ser Gln Cys Ser Gly Trp Gly Thr Ile Asn Ser Gly Gly Ile
        130                 135                 140

Cys Cys Pro Ala Val Leu Arg Tyr Val Thr Leu Asn Ile Thr Thr Asn
145                 150                 155                 160

Ala Phe Cys Asp Ala Val Tyr Thr Ser Asp Thr Ile Tyr Asp Asp Met
                165                 170                 175

Ile Cys Ala Thr Asp Asn Thr Gly Met Thr Asp Arg Asp Ser Cys Gln
            180                 185                 190

Gly Asp Ser Gly Gly Pro Leu Ser Val Lys Asp Gly Ser Gly Ile Phe
        195                 200                 205

Ser Leu Gly Gly Ile Val Ser Trp Gly Ile Gly Cys Ala Ser Gly Tyr
    210                 215                 220

Pro Gly Val Tyr Ser Arg Val Gly Phe His Ala Gly Trp Ile Thr Asp
225                 230                 235                 240

Thr Ile Thr Asn Asn
                245

<210> SEQ ID NO 2
<211> LENGTH: 246
<212> TYPE: PRT
<213> ORGANISM: Lumbricus rubellus

<400> SEQUENCE: 2

Met Glu Leu Pro Pro Gly Thr Lys Ile Val Gly Ile Glu Ala Arg
1               5                   10                  15

Pro Tyr Glu Phe Pro Trp Gln Val Ser Val Arg Arg Lys Ser Ser Asp
                20                  25                  30

Ser His Phe Cys Gly Gly Ser Ile Ile Asn Asp Arg Trp Val Val Cys
            35                  40                  45
```

```
Ala Ala His Cys Met Gln Gly Glu Ala Pro Ala Leu Val Ser Leu Val
 50                  55                  60

Val Gly Glu His Asp Arg Ser Ala Ala Ser Thr Val Arg Gln Thr His
 65                  70                  75                  80

Asp Val Asp Ser Ile Phe Val His Glu Asp Tyr Asn Ala Asn Thr Leu
                 85                  90                  95

Glu Asn Asp Val Ser Val Ile Lys Thr Ser Val Ala Ile Thr Phe Asp
            100                 105                 110

Ile Asn Val Gly Pro Ile Cys Ala Pro Asp Pro Ala Asn Asp Tyr Val
        115                 120                 125

Tyr Arg Lys Ser Gln Cys Ser Gly Trp Gly Thr Ile Asn Ser Gly Gly
130                 135                 140

Ile Cys Cys Pro Asn Val Leu Arg Tyr Val Thr Leu Asn Val Thr Thr
145                 150                 155                 160

Asn Gln Phe Cys Glu Asp Val Tyr Pro Leu Asn Ser Ile Tyr Asp Asp
                165                 170                 175

Met Ile Cys Ala Ser Asp Asn Thr Gly Gly Asn Asp Arg Asp Ser Cys
            180                 185                 190

Gln Gly Asp Ser Gly Gly Pro Leu Ser Val Lys Asp Gly Ser Gly Ile
        195                 200                 205

Phe Ser Leu Ile Gly Ile Val Ser Trp Gly Ile Gly Cys Ala Ser Gly
210                 215                 220

Tyr Pro Gly Val Tyr Ser Arg Val Gly Phe His Ala Ala Trp Ile Thr
225                 230                 235                 240

Asp Ile Ile Thr Asn Asn
                245

<210> SEQ ID NO 3
<211> LENGTH: 225
<212> TYPE: PRT
<213> ORGANISM: Eisenia fetida

<400> SEQUENCE: 3

Val Val Gly Gly Ser Asp Thr Thr Ile Gly Gln Tyr Pro His Gln Leu
1               5                   10                  15

Ser Leu Arg Val Thr Gly Ser His Ser Cys Gly Ala Ser Leu Ile Gly
            20                  25                  30

Thr Thr Arg Ala Val Thr Ala Ala His Cys Thr Gly Ser Ala Ile Ala
        35                  40                  45

Val Tyr Ser Ile Leu Gly Gly Thr Thr Asp Arg Thr Val Thr Asn Cys
 50                 55                  60

Ala Thr Cys Val Leu Arg Asp Leu Asn Phe Leu Asn Arg His Pro Ala
 65                 70                  75                  80

Tyr Asp Gly Asn Ala Pro Gly Tyr Pro Asn Asp Val Ala Val Ile Gly
                85                  90                  95

Phe Ala Ala Val Ala Thr Asn Thr Asn Leu Gln Ala Ile Ser Leu Ala
            100                 105                 110

Thr Pro Ser Asp Gly Asn Phe Ala Gly Asp Ser Cys Val Ile Thr Gly
        115                 120                 125

Trp Gly Gln Thr Gly Ser Ile Gly Gly Leu Pro Asp Ala Leu Gln Leu
130                 135                 140

Ala Thr Met Asn Val Leu Thr Asn Ala Asp Cys Thr Asn Thr Trp Gly
145                 150                 155                 160

Ala Val Arg Ile Asn Asp Gly His Ile Cys Val Ser Ala Ala Gly Arg
                165                 170                 175
```

```
Ser Ala Cys Ser Gly Asp Ser Gly Pro Leu Glu Cys Ser Asn Arg
            180                 185                 190

Leu Ala Gly Ala Thr Ser Trp Gly Glu Ala Ser Cys Asp Pro Ser Tyr
            195                 200                 205

Pro Ser Val Tyr Thr Arg Val Ser Tyr Phe Tyr Thr Trp Ile Ile Ala
210                 215                 220

Gln
225

<210> SEQ ID NO 4
<211> LENGTH: 236
<212> TYPE: PRT
<213> ORGANISM: Eisenia fetida

<400> SEQUENCE: 4

Ile Ile Gly Gly Ser Asn Ala Ser Pro Gly Glu Phe Pro Trp Gln Leu
1               5                   10                  15

Ser Gln Thr Arg Gly Gly Ser His Ser Cys Gly Ala Ser Leu Leu Asn
            20                  25                  30

Ala Leu Asn Gly Leu Ser Ala Ser His Cys Val Asp Gly Ala Ala Pro
        35                  40                  45

Gly Thr Ile Thr Val Ile Ala Gly Leu His Asp Arg Ser Gly Thr Pro
    50                  55                  60

Gly Ser Gln Glu Val Asp Ile Thr Gly Tyr Thr Met His Glu Asn Tyr
65                  70                  75                  80

Asn Gln Gly Thr Asn Thr Tyr Ala Asn Asp Ile Ala Ile Leu His Phe
                85                  90                  95

Ala Ser Ala Ile Asn Ile Gly Gly Asn Val Gln Ala Ala Leu Leu Pro
            100                 105                 110

Ala Asn Asn Asn Asp Tyr Ser Asp Leu Thr Cys Val Ile Ser Gly
        115                 120                 125

Trp Gly Arg Thr Gly Ser Ser Asn Val Leu Pro Asp Thr Leu Gln Lys
    130                 135                 140

Ala Ser Ile Gln Val Ile Gly Thr Thr Gln Cys Gln Ser Leu Met Gly
145                 150                 155                 160

Ser Ile Gly Asn Ile Trp Asp Asn His Ile Cys Leu Tyr Asp Asn Ala
                165                 170                 175

Asn Asn Val Gly Ser Cys Asn Gly Asp Ser Gly Gly Pro Leu Asn Cys
            180                 185                 190

Pro Asp Gly Gly Thr Arg Val Ala Gly Val Thr Ser Trp Gly Val Ser
        195                 200                 205

Ser Gly Ala Gly Asn Cys Leu Gln Thr Tyr Pro Ser Val Tyr Thr Arg
    210                 215                 220

Thr Ser Ala Tyr Leu Ser Trp Ile Ala Asn Asn Ser
225                 230                 235

<210> SEQ ID NO 5
<211> LENGTH: 242
<212> TYPE: PRT
<213> ORGANISM: Eisenia fetida

<400> SEQUENCE: 5

Val Ile Gly Gly Thr Asn Ala Ser Pro Gly Glu Phe Pro Trp Gln Leu
1               5                   10                  15

Ser Gln Gln Arg Gln Ser Gly Ser Trp Ser His Ser Cys Gly Ala Ser
            20                  25                  30
```

-continued

```
Leu Leu Ser Ser Thr Ser Ala Leu Ser Ala Ser His Cys Val Asp Gly
        35                  40                  45

Val Leu Pro Asn Asn Ile Arg Val Ile Ala Gly Leu Trp Gln Gln Ser
 50                  55                  60

Asp Thr Ser Gly Thr Gln Thr Ala Asn Val Asp Ser Tyr Thr Met His
 65                  70                  75                  80

Glu Asn Tyr Gly Ala Gly Thr Ala Ser Tyr Ser Asn Asp Ile Ala Ile
                 85                  90                  95

Leu His Leu Ala Thr Ser Ile Ser Leu Gly Gly Asn Ile Gln Ala Ala
            100                 105                 110

Val Leu Pro Ala Asn Asn Asn Asp Tyr Ala Gly Thr Thr Cys Val
            115                 120                 125

Ile Ser Gly Trp Gly Arg Thr Asp Gly Thr Asn Asn Leu Pro Asp Ile
130                 135                 140

Leu Gln Lys Ser Ser Ile Pro Val Ile Thr Thr Ala Gln Cys Thr Ala
145                 150                 155                 160

Ala Met Val Gly Val Gly Ala Asn Ile Trp Asp Asn His Ile Cys
                165                 170                 175

Val Gln Asp Pro Ala Gly Asn Thr Gly Ala Cys Asn Gly Asp Ser Gly
            180                 185                 190

Gly Pro Leu Asn Cys Pro Asp Gly Thr Arg Val Val Gly Val Thr
            195                 200                 205

Ser Trp Val Val Ser Ser Gly Leu Gly Ala Cys Leu Pro Asp Tyr Pro
210                 215                 220

Ser Val Tyr Thr Arg Val Ser Ala Tyr Leu Gly Trp Ile Gly Asp Asn
225                 230                 235                 240

Ser Arg

<210> SEQ ID NO 6
<211> LENGTH: 239
<212> TYPE: PRT
<213> ORGANISM: Eisenia fetida

<400> SEQUENCE: 6

Met Ile Val Gly Gly Ile Glu Ala Arg Pro Tyr Glu Phe Pro Trp Gln
 1               5                  10                  15

Val Ser Val Arg Arg Lys Ser Ser Asp Ser His Phe Cys Gly Gly Ser
                20                  25                  30

Ile Ile Asn Asp Arg Trp Val Val Cys Ala Ala His Cys Met Gln Gly
            35                  40                  45

Glu Ser Pro Ala Leu Val Ser Leu Val Val Gly Glu His Asp Ser Ser
 50                  55                  60

Ala Ala Ser Thr Val Arg Gln Thr His Asp Val Asp Ser Ile Phe Val
 65                  70                  75                  80

Asn Glu Asn Tyr Asp Pro Arg Thr Leu Glu Asn Asp Val Ser Val Ile
                 85                  90                  95

Lys Thr Ala Ile Ala Ile Thr Phe Asp Ile Asn Val Gly Pro Ile Cys
            100                 105                 110

Ala Pro Asp Pro Ala Asn Asp Tyr Val Tyr Arg Lys Ser Gln Cys Ser
            115                 120                 125

Gly Trp Gly Thr Ile Asn Ser Gly Gly Ile Cys Cys Pro Ala Val Leu
130                 135                 140

Arg Tyr Val Thr Leu Asn Ile Thr Asn Ala Phe Cys Asp Ala Val
145                 150                 155                 160
```

```
Tyr Thr Ser Asp Thr Ile Tyr Asp Asp Met Ile Cys Ala Thr Asp Asn
                165                 170                 175

Thr Gly Met Thr Asp Arg Asp Ser Cys Gln Gly Asp Ser Gly Gly Pro
            180                 185                 190

Leu Ser Val Lys Asp Gly Ser Gly Ile Phe Ser Leu Val Gly Ile Val
        195                 200                 205

Ser Trp Gly Ile Gly Cys Ala Ser Gly Tyr Pro Gly Val Tyr Ser Arg
    210                 215                 220

Val Gly Phe His Ala Gly Trp Ile Thr Asp Ile Ile Thr Asn Asn
225                 230                 235

<210> SEQ ID NO 7
<211> LENGTH: 242
<212> TYPE: PRT
<213> ORGANISM: Lumbricus bimastus

<400> SEQUENCE: 7

Val Ile Gly Gly Thr Asn Ala Ser Pro Gly Glu Phe Pro Trp Gln Leu
1               5                   10                  15

Ser Gln Gln Arg Gln Ser Gly Ser Trp Ser His Ser Cys Gly Ala Ser
            20                  25                  30

Leu Leu Ser Ser Thr Ser Ala Leu Ser Ala Ser His Cys Val Asp Gly
        35                  40                  45

Val Leu Pro Asn Asn Ile Arg Val Ile Ala Gly Leu Trp Gln Gln Ser
    50                  55                  60

Asp Thr Ser Gly Thr Gln Thr Ala Asn Val Asp Ser Tyr Thr Met His
65                  70                  75                  80

Glu Asn Tyr Gly Ala Gly Thr Ala Ser Tyr Ser Asn Asp Ile Ala Ile
                85                  90                  95

Leu His Leu Ala Thr Ser Ile Ser Leu Gly Asn Ile Gln Ala Ala
            100                 105                 110

Val Leu Pro Ala Asn Asn Asn Asn Asp Tyr Ala Gly Thr Thr Cys Val
        115                 120                 125

Ile Ser Gly Trp Gly Arg Thr Asp Gly Thr Asn Asn Leu Pro Asp Ile
    130                 135                 140

Leu Gln Lys Ser Ser Ile Pro Val Ile Thr Thr Ala Gln Cys Thr Ala
145                 150                 155                 160

Ala Met Val Gly Val Gly Gly Ala Asn Ile Trp Asp Asn His Ile Cys
                165                 170                 175

Val Gln Asp Pro Ala Gly Asn Thr Gly Ala Cys Asn Gly Asp Ser Gly
            180                 185                 190

Gly Pro Leu Asn Cys Pro Asp Gly Gly Thr Arg Val Val Gly Val Thr
        195                 200                 205

Ser Trp Val Val Ser Ser Gly Leu Gly Thr Cys Leu Pro Asp Tyr Pro
    210                 215                 220

Ser Val Tyr Thr Arg Val Ser Ala Tyr Leu Gly Trp Ile Gly Asp Asn
225                 230                 235                 240

Ser Arg

<210> SEQ ID NO 8
<211> LENGTH: 283
<212> TYPE: PRT
<213> ORGANISM: Lumbricus bimastus
```

```
<400> SEQUENCE: 8

Met Leu Leu Leu Ala Leu Ala Ser Leu Val Ala Val Gly Phe Ala Gln
 1               5                  10                  15

Pro Pro Val Trp Tyr Pro Gly Gly Gln Cys Gly Val Ser Gln Tyr Ser
            20                  25                  30

Asp Ala Gly Asp Met Glu Leu Pro Pro Gly Thr Lys Ile Val Gly Gly
         35                  40                  45

Ile Glu Ala Arg Pro Tyr Glu Phe Pro Trp Gln Val Ser Val Arg Arg
 50                  55                  60

Lys Ser Ser Asp Ser His Phe Cys Gly Gly Ser Ile Ile Asn Asp Arg
 65                  70                  75                  80

Trp Val Val Cys Ala Ala His Cys Met Gln Gly Glu Ser Pro Ala Leu
                 85                  90                  95

Val Ser Leu Val Val Gly Glu His Asp Ser Ser Ala Ala Ser Thr Val
            100                 105                 110

Arg Gln Thr His Asp Val Asp Ser Ile Phe Val His Glu Asp Tyr Asn
         115                 120                 125

Gly Asn Thr Phe Glu Asn Asp Val Ser Val Ile Lys Thr Val Asn Ala
130                 135                 140

Ile Ala Ile Asp Ile Asn Val Gly Pro Ile Cys Ala Pro Asp Pro Ala
145                 150                 155                 160

Asn Asp Tyr Val Tyr Arg Lys Ser Gln Cys Ser Gly Trp Gly Thr Ile
                165                 170                 175

Asn Ser Gly Gly Val Cys Cys Pro Asn Val Leu Arg Tyr Val Thr Leu
            180                 185                 190

Asn Val Thr Thr Asn Ala Phe Cys Asp Asp Ile Tyr Ser Pro Leu Tyr
        195                 200                 205

Thr Ile Thr Ser Asp Met Ile Cys Ala Thr Asp Asn Thr Gly Gln Asn
210                 215                 220

Glu Arg Asp Ser Cys Gln Gly Asp Ser Gly Pro Leu Ser Val Lys
225                 230                 235                 240

Asp Gly Ser Gly Ile Phe Ser Leu Ile Gly Ile Val Ser Trp Gly Ile
                245                 250                 255

Gly Cys Ala Ser Gly Tyr Pro Gly Val Tyr Ala Arg Val Gly Ser Gln
            260                 265                 270

Thr Gly Trp Ile Thr Asp Ile Ile Thr Asn Asn
        275                 280

<210> SEQ ID NO 9
<211> LENGTH: 283
<212> TYPE: PRT
<213> ORGANISM: Lumbricus rubellus

<400> SEQUENCE: 9

Met Leu Leu Leu Ala Leu Ala Ser Leu Val Ala Val Gly Phe Ala Gln
 1               5                  10                  15

Pro Pro Val Trp Tyr Pro Gly Gly Gln Cys Ser Val Ser Gln Tyr Ser
            20                  25                  30

Asp Ala Gly Asp Met Glu Leu Pro Pro Gly Thr Lys Ile Val Gly Gly
         35                  40                  45

Ile Glu Ala Arg Pro Tyr Glu Phe Pro Trp Gln Val Ser Val Arg Arg
 50                  55                  60

Lys Ser Ser Asp Ser His Phe Cys Gly Gly Ser Ile Ile Asn Asp Arg
 65                  70                  75                  80
```

-continued

Trp Val Val Cys Ala His Cys Met Gln Gly Glu Ser Pro Ala Leu
            85                  90                  95

Val Ser Leu Val Val Gly Glu His Asp Ser Ser Ala Ala Ser Thr Val
        100                 105                 110

Arg Gln Thr His Asp Val Asp Ser Ile Phe Val His Glu Asp Tyr Asn
            115                 120                 125

Gly Asn Thr Phe Glu Asn Asp Val Ser Val Ile Lys Thr Val Asn Ala
        130                 135                 140

Ile Ala Ile Asp Ile Asn Asp Gly Pro Ile Cys Ala Pro Asp Pro Ala
145                 150                 155                 160

Asn Asp Tyr Val Tyr Arg Lys Ser Gln Cys Ser Gly Trp Gly Thr Ile
                165                 170                 175

Asn Ser Gly Gly Val Cys Cys Pro Asn Val Leu Arg Tyr Val Thr Leu
            180                 185                 190

Asn Val Thr Thr Asn Ala Phe Cys Asp Asp Ile Tyr Ser Pro Leu Tyr
        195                 200                 205

Thr Ile Thr Ser Asp Met Ile Cys Ala Thr Asp Asn Thr Gly Gln Asn
    210                 215                 220

Glu Arg Asp Ser Cys Gln Gly Asp Ser Gly Gly Pro Leu Ser Val Lys
225                 230                 235                 240

Asp Gly Asn Gly Ile Phe Ser Leu Ile Gly Ile Val Ser Trp Gly Ile
                245                 250                 255

Gly Cys Ala Ser Gly Tyr Pro Gly Val Tyr Ala Arg Val Gly Ser Gln
            260                 265                 270

Thr Gly Trp Ile Thr Asp Ile Ile Thr Asn Asn
        275                 280

<210> SEQ ID NO 10
<211> LENGTH: 246
<212> TYPE: PRT
<213> ORGANISM: Lumbricus bimastus

<400> SEQUENCE: 10

Met Glu Leu Pro Pro Gly Thr Lys Ile Val Gly Gly Ile Glu Ala Arg
1               5                   10                  15

Pro Tyr Glu Phe Pro Trp Gln Val Ser Val Arg Arg Lys Ser Ser Asp
            20                  25                  30

Ser His Phe Cys Gly Gly Ser Ile Ile Asn Asp Arg Trp Val Val Cys
        35                  40                  45

Ala Ala His Cys Met Gln Gly Glu Ala Pro Ala Leu Val Ser Leu Val
    50                  55                  60

Val Gly Glu His Asp Arg Ser Ala Ala Ser Thr Val Arg Gln Thr His
65                  70                  75                  80

Asp Val Asp Ser Ile Phe Val His Glu Asp Tyr Asn Thr Asn Thr Leu
                85                  90                  95

Glu Asn Asp Val Ser Val Ile Lys Thr Ser Val Ala Ile Thr Phe Asp
            100                 105                 110

Ile Asn Val Gly Pro Ile Cys Ala Pro Asp Pro Ala Asn Asp Tyr Val
        115                 120                 125

Tyr Arg Lys Ser Gln Cys Ser Gly Trp Gly Thr Ile Asn Ser Gly Gly
    130                 135                 140

Ile Cys Cys Pro Asn Val Leu Arg Tyr Val Thr Leu Asn Asp Thr Thr
145                 150                 155                 160

Asn Gln Tyr Cys Glu Asp Val Tyr Pro Leu Asn Ser Ile Tyr Asp Asp
                165                 170                 175

```
Met Ile Cys Ala Ser Asp Asn Thr Gly Gly Asn Asp Arg Asp Ser Cys
            180                 185                 190

Gln Gly Asp Ser Gly Gly Pro Leu Ser Val Lys Asp Gly Ser Gly Ile
            195                 200                 205

Phe Ser Leu Ile Gly Ile Val Ser Trp Gly Ile Gly Cys Ala Ser Gly
            210                 215                 220

Tyr Pro Gly Val Tyr Ser Arg Val Gly Phe His Ala Ala Trp Ile Thr
225                 230                 235                 240

Asp Ile Ile Thr Asn Asn
                245

<210> SEQ ID NO 11
<211> LENGTH: 246
<212> TYPE: PRT
<213> ORGANISM: Lumbricus bimastus

<400> SEQUENCE: 11

Met Glu Leu Pro Pro Gly Thr Lys Ile Val Gly Gly Ile Glu Ala Arg
1               5                   10                  15

Pro Tyr Glu Phe Pro Trp Gln Val Ser Val Arg Arg Lys Ser Ser Asp
                20                  25                  30

Ser His Phe Cys Gly Gly Ser Ile Ile Asn Asp Arg Trp Val Val Cys
            35                  40                  45

Ala Ala His Cys Met Gln Gly Glu Ala Pro Ala Leu Val Ser Leu Val
        50                  55                  60

Val Gly Glu His Asp Arg Ser Ala Ala Ser Thr Val Arg Gln Thr His
65                  70                  75                  80

Asp Val Asp Ser Ile Phe Val His Glu Asp Tyr Asn Thr Asn Thr Leu
                85                  90                  95

Glu Asn Asp Val Ser Val Ile Lys Thr Ser Val Ala Ile Thr Phe Asp
                100                 105                 110

Ile Asn Val Gly Pro Ile Cys Ala Pro Asp Pro Ala Asn Asp Tyr Val
            115                 120                 125

Tyr Arg Lys Ser Gln Cys Ser Gly Trp Gly Thr Ile Asn Ser Gly Gly
        130                 135                 140

Ile Cys Cys Pro Asn Val Leu Arg Tyr Val Thr Leu Asn Asp Thr Thr
145                 150                 155                 160

Asn Gln Tyr Cys Glu Asp Val Tyr Pro Leu Asn Ser Ile Tyr Asp Asp
                165                 170                 175

Met Ile Cys Ala Ser Asp Asn Thr Gly Gly Asn Asp Arg Asp Ser Cys
            180                 185                 190

Gln Gly Asp Ser Gly Gly Pro Leu Ser Val Lys Asp Gly Ser Gly Ile
            195                 200                 205

Phe Ser Leu Ile Gly Ile Val Ser Trp Gly Ile Gly Cys Ala Ser Gly
            210                 215                 220

Tyr Pro Gly Val Tyr Ser Arg Val Gly Phe His Ala Ala Trp Ile Thr
225                 230                 235                 240

Asp Ile Ile Thr Asn Asn
                245

<210> SEQ ID NO 12
<211> LENGTH: 245
<212> TYPE: PRT
<213> ORGANISM: Eisenia fetida
```

```
<400> SEQUENCE: 12

Met Glu Leu Pro Pro Gly Lys Ile Val Gly Gly Ile Glu Ala Gly Pro
1               5                   10                  15

Tyr Glu Phe Pro Trp Gln Val Ser Val Arg Arg Lys Pro Ser Asp Ser
            20                  25                  30

His Phe Cys Gly Gly Ser Ile Ile Asn Asp Arg Trp Val Val Cys Ala
        35                  40                  45

Ala His Cys Met Gln Gly Glu Ser Pro Ala Leu Val Ser Leu Val Val
    50                  55                  60

Gly Glu His Asp Ser Ser Ala Ala Ser Thr Val Arg Gln Thr His Asp
65                  70                  75                  80

Val Asp Ser Ile Phe Val Asn Glu Asn Tyr Asp Pro Arg Thr Leu Glu
                85                  90                  95

Asn Asp Val Ser Val Ile Lys Thr Ala Ile Ala Ile Thr Phe Asp Ile
            100                 105                 110

Asn Val Gly Pro Ile Cys Ala Pro Asp Pro Ala Asn Asp Tyr Val Tyr
        115                 120                 125

Arg Lys Ser Gln Cys Ser Gly Trp Gly Thr Ile Asn Ser Gly Gly Ile
    130                 135                 140

Cys Cys Pro Ala Val Leu Arg Tyr Val Thr Leu Asn Ile Thr Thr Asn
145                 150                 155                 160

Ala Phe Cys Asp Ala Val Tyr Thr Ser Asp Thr Ile Tyr Asp Asp Met
                165                 170                 175

Ile Cys Ala Thr Asp Asn Thr Gly Met Thr Asp Arg Asp Ser Cys Gln
            180                 185                 190

Gly Asp Ser Gly Gly Pro Leu Ser Val Lys Asp Gly Ser Gly Ile Phe
        195                 200                 205

Ser Leu Val Gly Ile Val Ser Trp Gly Ile Gly Cys Ala Ser Gly Tyr
    210                 215                 220

Pro Gly Val Tyr Ser Arg Val Gly Phe His Ala Gly Trp Ile Thr Asp
225                 230                 235                 240

Thr Ile Thr Asn Asn
                245

<210> SEQ ID NO 13
<211> LENGTH: 246
<212> TYPE: PRT
<213> ORGANISM: Eisenia fetida

<400> SEQUENCE: 13

Met Glu Leu Pro Pro Gly Thr Lys Ile Val Gly Gly Ile Glu Ala Arg
1               5                   10                  15

Pro Tyr Glu Phe Pro Trp Gln Val Ser Val Arg Arg Lys Ser Thr Asp
            20                  25                  30

Ser His Phe Cys Gly Gly Ser Ile Ile Asn Asp Arg Trp Val Val Cys
        35                  40                  45

Ala Ala His Cys Met Gln Gly Glu Ser Pro Ala Leu Val Ser Leu Val
    50                  55                  60

Val Gly Glu His Asp Ser Ser Ala Ala Ser Thr Val Arg Gln Thr His
65                  70                  75                  80

Asp Val Asp Ser Ile Phe Val Asn Glu Asn Tyr Asn Pro Arg Thr Leu
                85                  90                  95
```

-continued

Glu Asn Asp Val Ser Val Ile Lys Thr Ala Ile Ala Ile Thr Phe Asp
                100                 105                 110

Ile Asn Val Gly Pro Ile Cys Ala Pro Asp Pro Ala Asn Asp Tyr Val
            115                 120                 125

Tyr Arg Lys Ser Gln Cys Ser Gly Trp Gly Ser Ile Asn Ser Gly Gly
        130                 135                 140

Ile Cys Cys Pro Ala Val Leu Arg Tyr Val Thr Leu Asn Ile Thr Thr
145                 150                 155                 160

Asn Ala Phe Cys Asp Ala Val Tyr Thr Ser Asp Thr Ile Tyr Asp Asp
                165                 170                 175

Met Ile Cys Ala Thr Asp Asn Thr Gly Met Thr Asp Arg Asp Ser Cys
            180                 185                 190

Gln Gly Asp Ser Gly Gly Pro Leu Ser Val Lys Asp Gly Ser Gly Ile
        195                 200                 205

Phe Ser Leu Val Gly Ile Val Ser Trp Gly Ile Gly Cys Ala Ser Gly
210                 215                 220

Tyr Pro Gly Val Tyr Ser Arg Val Gly Phe His Ala Gly Trp Ile Thr
225                 230                 235                 240

Asp Thr Ile Thr Asn Asn
                245

<210> SEQ ID NO 14
<211> LENGTH: 242
<212> TYPE: PRT
<213> ORGANISM: Eisenia fetida

<400> SEQUENCE: 14

Val Ile Gly Gly Thr Asn Ala Ser Pro Gly Glu Phe Pro Trp Gln Leu
1               5                   10                  15

Ser Gln Gln Arg Gln Ser Gly Ser Trp Ser His Ser Cys Gly Ala Ser
            20                  25                  30

Leu Leu Ser Ser Thr Ser Ala Leu Ser Ala Ser His Cys Val Asp Gly
        35                  40                  45

Val Leu Pro Asn Asn Ile Arg Val Ile Ala Gly Leu Trp Gln Gln Ser
    50                  55                  60

Asp Thr Ser Gly Thr Gln Thr Ala Asn Val Asp Ser Tyr Thr Met His
65                  70                  75                  80

Glu Asn Tyr Gly Ala Gly Thr Ala Ser Tyr Ser Asn Asp Ile Ala Ile
                85                  90                  95

Leu His Leu Ala Thr Ser Ile Ser Leu Gly Gly Asn Ile Gln Ala Ala
            100                 105                 110

Val Leu Pro Ala Asn Asn Asn Asp Tyr Ala Gly Thr Thr Cys Val
        115                 120                 125

Ile Ser Gly Trp Gly Arg Thr Asp Gly Thr Asn Asn Leu Pro Asp Ile
    130                 135                 140

Leu Gln Lys Ser Ser Ile Pro Val Ile Thr Thr Ala Gln Cys Thr Ala
145                 150                 155                 160

Ala Met Val Gly Val Gly Gly Ala Asn Ile Trp Asp Asn His Ile Cys
                165                 170                 175

Val Gln Asp Pro Ala Gly Asn Thr Gly Ala Cys Asn Gly Asp Ser Gly
            180                 185                 190

Gly Pro Leu Asn Cys Pro Asp Gly Gly Thr Arg Val Val Gly Val Thr
        195                 200                 205

Ser Trp Val Val Ser Ser Gly Leu Gly Ala Cys Leu Pro Asp Tyr Pro
        210                 215                 220

Ser Val Tyr Thr Arg Val Ser Ala His Leu Gly Trp Ile Gly Asp Asn
225                 230                 235                 240

Ser Arg

<210> SEQ ID NO 15
<211> LENGTH: 239
<212> TYPE: PRT
<213> ORGANISM: Eisenia fetida

<400> SEQUENCE: 15

Ile Val Gly Gly Ile Glu Ala Arg Pro Tyr Glu Phe Pro Trp Gln Val
1               5                   10                  15

Ser Val Arg Arg Lys Ser Ser Asp Ser His Phe Cys Gly Gly Ser Ile
                20                  25                  30

Ile Asn Asp Arg Trp Val Val Cys Ala Ala His Cys Met Gln Gly Glu
            35                  40                  45

Ser Pro Ala Leu Val Ser Leu Val Val Gly Glu His Asp Ser Ser Ala
        50                  55                  60

Ala Ser Thr Val Arg Gln Thr His Asp Val Asp Ser Ile Phe Val His
65                  70                  75                  80

Glu Asp Tyr Asn Gly Asn Thr Phe Glu Asn Asp Val Ser Val Ile Lys
                85                  90                  95

Thr Val Asn Ala Ile Ala Ile Asp Ile Asn Val Gly Pro Ile Cys Ala
                100                 105                 110

Pro Asp Pro Ala Asn Asp Tyr Val Tyr Arg Lys Ser Gln Cys Ser Gly
            115                 120                 125

Trp Gly Thr Val Asn Ser Gly Gly Val Cys Cys Pro Asn Val Leu Arg
130                 135                 140

Tyr Val Thr Leu Asn Val Thr Thr Asn Ala Phe Cys Asp Asp Ile Tyr
145                 150                 155                 160

Ser Pro Leu Tyr Thr Ile Thr Ser Asp Met Ile Cys Ala Thr Asp Asn
                165                 170                 175

Thr Gly Gln Asn Glu Arg Asp Ser Cys Gln Gly Asp Ser Gly Gly Pro
            180                 185                 190

Leu Ser Val Lys Asp Gly Ser Gly Ile Phe Ser Leu Ile Gly Ile Val
        195                 200                 205

Ser Trp Gly Ile Gly Cys Ala Ser Gly Tyr Pro Gly Val Tyr Ala Arg
210                 215                 220

Val Gly Ser Gln Thr Gly Trp Ile Thr Asp Ile Ile Thr Asn Asn
225                 230                 235

<210> SEQ ID NO 16
<211> LENGTH: 238
<212> TYPE: PRT
<213> ORGANISM: Eisenia fetida

<400> SEQUENCE: 16

Ile Val Gly Gly Ile Glu Ala Arg Pro Tyr Glu Phe Pro Trp Gln Val
1               5                   10                  15

Ser Val Arg Arg Lys Ser Ser Asp Ser His Phe Cys Gly Gly Ser Ile
                20                  25                  30

Ile Asn Asp Arg Trp Val Val Cys Ala Ala His Cys Met Gln Gly Glu
            35                  40                  45

Ser Pro Ala Leu Val Ser Leu Val Val Gly Glu His Asp Ser Ser Ala
        50                  55                  60

```
Ala Ser Thr Val Arg Gln Thr His Asp Val Asp Ser Ile Phe Val Asn
 65                  70                  75                  80

Glu Asn Tyr Asp Pro Arg Thr Leu Glu Asn Asp Val Ser Val Ile Lys
             85                  90                  95

Thr Ala Ile Ala Ile Thr Phe Asp Ile Asn Val Gly Pro Ile Cys Ala
         100                 105                 110

Pro Asp Pro Ala Asn Asp Tyr Val Tyr Arg Lys Ser Gln Cys Ser Gly
         115                 120                 125

Trp Gly Thr Ile Asn Ser Gly Ile Cys Cys Pro Ala Val Leu Arg
         130                 135                 140

Tyr Val Thr Leu Asn Ile Thr Thr Asn Ala Phe Cys Asp Ala Val Tyr
145                 150                 155                 160

Thr Ser Asp Thr Ile Tyr Asp Asp Met Ile Cys Ala Thr Asp Asn Thr
                 165                 170                 175

Gly Met Thr Asp Arg Asp Ser Cys Gln Gly Asp Ser Gly Gly Pro Leu
             180                 185                 190

Ser Val Lys Asp Gly Ser Gly Ile Phe Ser Leu Val Gly Ile Val Ser
         195                 200                 205

Trp Gly Ile Gly Cys Ala Ser Gly Tyr Pro Gly Val Tyr Ser Arg Val
210                 215                 220

Gly Phe His Ala Gly Trp Ile Thr Asp Thr Ile Thr Asn Asn
225                 230                 235

<210> SEQ ID NO 17
<211> LENGTH: 242
<212> TYPE: PRT
<213> ORGANISM: Eisenia fetida

<400> SEQUENCE: 17

Val Ile Gly Gly Thr Asn Ala Ser Pro Gly Glu Phe Pro Trp Gln Leu
1               5                   10                  15

Ser Gln Gln Arg Gln Ser Gly Ser Trp Ser His Ser Cys Gly Ala Ser
             20                  25                  30

Leu Leu Ser Ser Thr Ser Ala Leu Ser Ala Ser His Cys Val Asp Gly
         35                  40                  45

Val Leu Pro Asn Asn Ile Arg Val Ile Ala Gly Leu Trp Gln Gln Ser
 50                  55                  60

Asp Thr Ser Gly Thr Gln Thr Ala Asn Val Asp Ser Tyr Thr Met His
 65                  70                  75                  80

Glu Asn Tyr Gly Ala Gly Thr Ala Ser Tyr Ser Asn Asp Ile Ala Ile
             85                  90                  95

Leu His Leu Ala Thr Ser Ile Ser Leu Gly Gly Asn Ile Gln Ala Ala
         100                 105                 110

Val Leu Pro Ala Asn Asn Asn Asp Tyr Ala Gly Thr Thr Cys Val
         115                 120                 125

Ile Ser Gly Trp Gly Arg Thr Asp Gly Thr Asn Asn Leu Pro Asp Ile
130                 135                 140

Leu Gln Lys Ser Ser Ile Pro Val Ile Thr Thr Ala Gln Cys Thr Ala
145                 150                 155                 160

Ala Met Val Gly Val Gly Ala Asn Ile Trp Asp Asn His Ile Cys
         165                 170                 175

Val Gln Asp Pro Ala Gly Asn Thr Gly Ala Cys Asn Gly Asp Ser Gly
         180                 185                 190

Gly Pro Leu Asn Cys Pro Asp Gly Gly Thr Arg Val Val Gly Val Thr
         195                 200                 205
```

```
Ser Trp Val Val Ser Ser Gly Leu Gly Ala Cys Leu Pro Asp Tyr Pro
    210                 215                 220

Ser Val Tyr Thr Arg Val Ser Ala Tyr Leu Gly Trp Ile Gly Asp Asn
225                 230                 235                 240

Ser Arg

<210> SEQ ID NO 18
<211> LENGTH: 235
<212> TYPE: PRT
<213> ORGANISM: Eisenia fetida

<400> SEQUENCE: 18

Ile Gly Gly Thr Asp Ala Ser Pro Gly Glu Phe Pro Trp Gln Leu Ser
1               5                   10                  15

Gln Thr Arg Gly Gly Ser His Ser Cys Gly Ala Ser Leu Leu Asn Ala
            20                  25                  30

Leu Asn Gly Leu Ser Ala Ser His Cys Val Asp Gly Ala Ala Pro Gly
        35                  40                  45

Thr Ile Thr Val Ile Ala Gly Leu His Asp Arg Ser Gly Thr Pro Gly
    50                  55                  60

Ser Gln Glu Val Asp Ile Thr Gly Tyr Thr Met His Glu Asn Tyr Asn
65                  70                  75                  80

Gln Gly Thr Asn Thr Tyr Ala Asn Asp Ile Ala Ile Leu His Phe Ala
                85                  90                  95

Ser Ala Ile Asn Ile Gly Gly Asn Val Gln Ala Ala Leu Leu Pro Ala
            100                 105                 110

Asn Asn Asn Asn Asp Tyr Asn Gly Leu Thr Cys Val Ile Ser Gly Trp
        115                 120                 125

Gly Arg Thr Gly Ser Ser Asn Val Leu Pro Asp Thr Leu Gln Lys Ala
    130                 135                 140

Ser Ile Glu Val Ile Gly Thr Thr Gln Cys Gln Ser Leu Met Gly Ser
145                 150                 155                 160

Ile Gly Asn Ile Trp Asp Asn His Ile Cys Leu Tyr Asp Asn Ala Asn
                165                 170                 175

Asn Val Gly Ser Cys Asn Gly Asp Ser Gly Gly Pro Leu Asn Cys Pro
            180                 185                 190

Asp Gly Gly Thr Arg Val Ala Gly Val Thr Ser Trp Gly Val Ser Ser
        195                 200                 205

Gly Ala Gly Asn Cys Leu Gln Thr Tyr Pro Ser Val Tyr Thr Arg Thr
    210                 215                 220

Ser Ala Tyr Leu Ser Trp Ile Ala Asn Asn Ser
225                 230                 235

<210> SEQ ID NO 19
<211> LENGTH: 238
<212> TYPE: PRT
<213> ORGANISM: Eisenia fetida

<400> SEQUENCE: 19

Val Ile Gly Gly Thr Asp Ala Ala Pro Gly Glu Phe Pro Trp Gln Leu
1               5                   10                  15

Ser Gln Thr Arg Gly Gly Ser His Ser Cys Gly Ala Ser Leu Leu Ser
            20                  25                  30

Ser Asn Ser Gly Leu Ser Ala Ser His Cys Val Asp Gly Ala Leu Pro
        35                  40                  45

Gly Ser Ile Thr Val Ile Ala Gly Leu His Asp Arg Ser Gly Thr Pro
    50                  55                  60
```

```
Gly Ser Gln Glu Val Asp Ile Thr Gly Tyr Thr Met His Glu Glu Tyr
65                  70                  75                  80

Leu Thr Gly Ile Tyr Thr Tyr Ser Asn Asp Ile Ser Ile Leu Asn Phe
                85                  90                  95

Ala Thr Pro Ile Thr Ile Gly Asn Ile Gln Pro Ala Thr Leu Pro
            100                 105                 110

Ala Asp Asn Ser Asn Asn Tyr Leu Gly Leu Thr Cys Val Ile Ser Gly
            115                 120                 125

Trp Gly Arg Thr Ser Ser Ser Asn Ile Leu Pro Asp Thr Leu Gln Lys
            130                 135                 140

Ala Ser Ile Gln Val Ile Gly Thr Asp Glu Cys Gln Thr Leu Val Asp
145                 150                 155                 160

Asn Val Leu Gly Cys Arg Ile Trp Asp Asn His Ile Cys Ile Tyr Asp
                165                 170                 175

Gln Ala Asn Ser Val Gly Ser Cys Asn Gly Asp Ser Gly Gly Pro Leu
            180                 185                 190

Asn Cys Pro Asp Gly Thr Thr Val Ala Gly Ile Thr Ser Trp Gly
            195                 200                 205

Ile Ser Ser Gly Gly Asp Cys Leu Gln Asp Tyr Pro Ser Val Tyr Thr
210                 215                 220

Arg Thr Ser Ala Tyr Leu Asp Trp Ile Ala Ala Asn Thr Pro
225                 230                 235

<210> SEQ ID NO 20
<211> LENGTH: 239
<212> TYPE: PRT
<213> ORGANISM: Lumbricus rubellus

<400> SEQUENCE: 20

Ile Val Gly Gly Ile Glu Ala Arg Pro Tyr Glu Phe Pro Trp Gln Val
1               5                   10                  15

Ser Val Arg Arg Lys Ser Ser Asp Ser His Phe Cys Gly Gly Ser Ile
            20                  25                  30

Ile Asn Asp Arg Trp Val Val Cys Ala Ala His Cys Met Gln Gly Glu
            35                  40                  45

Ser Pro Ala Leu Val Ser Leu Val Val Gly Glu His Asp Ser Ser Ala
50                  55                  60

Ala Ser Thr Val Arg Gln Thr His Asp Val Asp Ser Ile Phe Val His
65                  70                  75                  80

Glu Asp Tyr Asn Gly Asn Thr Phe Glu Asn Asp Val Ser Val Ile Lys
                85                  90                  95

Thr Val Asn Ala Ile Ala Ile Asp Ile Asn Asp Gly Pro Ile Cys Ala
            100                 105                 110

Pro Asp Pro Ala Asn Asp Tyr Val Tyr Arg Lys Ser Gln Cys Ser Gly
            115                 120                 125

Trp Gly Thr Ile Asn Ser Gly Gly Val Cys Cys Pro Asn Val Leu Arg
            130                 135                 140

Tyr Val Thr Leu Asn Val Thr Asn Ala Phe Cys Asp Asp Ile Tyr
145                 150                 155                 160

Ser Pro Leu Tyr Thr Ile Thr Ser Asp Met Ile Cys Ala Thr Asp Asn
                165                 170                 175

Thr Gly Gln Asn Glu Arg Asp Ser Cys Gln Gly Asp Ser Gly Gly Pro
            180                 185                 190

Leu Ser Val Lys Asp Gly Ser Gly Ile Phe Ser Leu Ile Gly Ile Val
            195                 200                 205
```

Ser Trp Gly Ile Gly Cys Ala Ser Gly Tyr Pro Val Tyr Ala Arg
210                 215                 220

Val Gly Ser Gln Thr Gly Trp Ile Thr Asp Ile Ile Thr Asn Asn
225                 230                 235

<210> SEQ ID NO 21
<211> LENGTH: 239
<212> TYPE: PRT
<213> ORGANISM: Eisenia fetida

<400> SEQUENCE: 21

Ile Val Gly Gly Ile Glu Ala Arg Pro Tyr Glu Phe Pro Trp Gln Val
1               5                   10                  15

Ser Val Arg Arg Lys Ser Ser Asp Ser His Phe Cys Gly Gly Ser Ile
                20                  25                  30

Ile Asn Asp Arg Trp Val Val Cys Ala Ala His Cys Met Gln Gly Glu
            35                  40                  45

Ser Pro Ala Leu Val Ser Leu Val Val Gly Glu His Asp Ser Ser Ala
        50                  55                  60

Ala Ser Thr Val Arg Gln Thr His Asp Val Asp Ser Ile Phe Val His
65                  70                  75                  80

Glu Asp Tyr Asn Gly Asn Thr Phe Glu Asn Asp Val Ser Val Ile Lys
                85                  90                  95

Thr Val Asn Ala Ile Ala Ile Asp Ile Asn Val Gly Pro Ile Cys Ala
            100                 105                 110

Pro Asp Pro Ala Asn Asp Tyr Val Tyr Arg Lys Ser Gln Cys Ser Gly
        115                 120                 125

Trp Gly Thr Val Asn Ser Gly Gly Val Cys Cys Pro Asn Val Leu Arg
130                 135                 140

Tyr Val Thr Leu Asn Val Thr Thr Asn Ala Phe Cys Asp Asp Ile Tyr
145                 150                 155                 160

Ser Pro Leu Tyr Thr Ile Thr Ser Asp Met Ile Cys Ala Thr Asp Asn
                165                 170                 175

Thr Gly Gln Asn Glu Arg Asp Ser Cys Gln Gly Asp Ser Gly Gly Pro
            180                 185                 190

Leu Ser Val Lys Asp Gly Ser Gly Ile Phe Ser Leu Ile Gly Ile Val
        195                 200                 205

Ser Trp Gly Ile Gly Cys Ala Ser Gly Tyr Pro Val Tyr Ala Arg
210                 215                 220

Val Gly Ser Gln Thr Gly Trp Ile Thr Asp Ile Ile Thr Asn Asn
225                 230                 235

<210> SEQ ID NO 22
<211> LENGTH: 238
<212> TYPE: PRT
<213> ORGANISM: Lumbricus rubellus

<400> SEQUENCE: 22

Ile Val Gly Gly Ile Glu Ala Arg Pro Tyr Glu Phe Pro Trp Gln Val
1               5                   10                  15

Ser Val Arg Arg Lys Ser Ser Asp Ser His Phe Cys Gly Gly Ser Ile
                20                  25                  30

Ile Asn Asp Arg Trp Val Val Cys Ala Ala His Cys Met Gln Gly Glu
            35                  40                  45

Ala Pro Ala Leu Val Ser Leu Val Val Gly Glu His Asp Arg Ser Ala
        50                  55                  60

```
Ala Ser Ala Val Arg Gln Thr His Asp Val Asp Ser Ile Phe Val His
 65                  70                  75                  80

Glu Asp Tyr Asn Thr Asn Leu Glu Asn Asp Val Ser Val Ile Lys
                 85                  90                  95

Thr Ser Val Ala Ile Thr Phe Asp Ile Asn Val Gly Pro Ile Cys Ala
            100                 105                 110

Pro Asp Pro Ala Gln Gln Tyr Val Tyr Arg Lys Ser Gln Cys Ser Gly
            115                 120                 125

Trp Gly Thr Ile Asn Ser Gly Gly Ile Cys Cys Pro Asn Ile Leu Arg
            130                 135                 140

Tyr Val Thr Leu Asn Val Thr Thr Asn Gln Phe Cys Glu Asp Val Tyr
145                 150                 155                 160

Pro Leu Asn Ser Ile Phe Asp Asp Met Ile Cys Ala Ser Asp Asn Thr
                165                 170                 175

Gly Gly Asn Asp Arg Asp Ser Cys Gln Gly Asp Ser Gly Gly Pro Leu
            180                 185                 190

Ser Val Lys Asp Gly Ser Gly Ile Phe Ser Leu Ile Gly Ile Val Ser
            195                 200                 205

Trp Gly Ile Gly Cys Ala Ser Gly Tyr Pro Gly Val Tyr Ser Arg Val
            210                 215                 220

Gly Phe His Thr Ala Trp Ile Thr Asp Ile Ile Thr Asn Asn
225                 230                 235

<210> SEQ ID NO 23
<211> LENGTH: 239
<212> TYPE: PRT
<213> ORGANISM: Lumbricus rubellus

<400> SEQUENCE: 23

Ile Val Gly Gly Ile Glu Ala Arg Pro Tyr Glu Phe Pro Trp Gln Val
  1               5                  10                  15

Ser Val Arg Arg Lys Ser Ser Asp Ser His Phe Cys Gly Gly Ser Ile
                 20                  25                  30

Ile Asn Asp His Trp Val Val Cys Ala Ala His Cys Met Gln Gly Glu
             35                  40                  45

Ser Pro Ala Leu Val Ser Leu Val Val Gly Glu His Asp Ser Ser Ala
 50                  55                  60

Ala Ser Thr Val Arg Gln Thr His Asp Val Asp Ser Ile Phe Val His
 65                  70                  75                  80

Glu Asp Tyr Asn Gly Asn Thr Phe Glu Asn Asp Val Ser Val Ile Lys
                 85                  90                  95

Thr Val Asn Ala Ile Ala Ile Asp Ile Asn Val Gly Pro Ile Cys Ala
            100                 105                 110

Pro Asp Pro Ala Asn Asp Tyr Val Tyr Arg Lys Ser Gln Cys Ser Gly
            115                 120                 125

Trp Gly Thr Ile Asn Ser Gly Gly Val Cys Cys Pro Asn Val Leu Arg
            130                 135                 140

Tyr Val Thr Leu Asn Val Thr Asn Ala Phe Cys Asp Asp Ile Tyr
145                 150                 155                 160

Ser Pro Leu Tyr Thr Ile Thr Ser Asp Met Ile Cys Ala Thr Asp Asn
                165                 170                 175

Thr Gly Gln Asn Glu Arg Asp Ser Cys Gln Gly Asp Ser Gly Gly Pro
            180                 185                 190

Leu Ser Val Lys Asp Gly Ser Gly Ile Phe Ser Leu Ile Gly Ile Val
            195                 200                 205
```

Ser Trp Gly Ile Gly Cys Ala Ser Gly Tyr Pro Val Tyr Ala Arg
210                 215                 220

Val Gly Ser Gln Thr Gly Trp Ile Thr Asp Ile Ile Thr Asn Asn
225                 230                 235

<210> SEQ ID NO 24
<211> LENGTH: 238
<212> TYPE: PRT
<213> ORGANISM: Eisenia fetida

<400> SEQUENCE: 24

Val Ile Gly Gly Thr Asp Ala Ala Pro Gly Glu Phe Pro Trp Gln Leu
1               5                   10                  15

Ser Gln Thr Arg Gly Gly Ser His Ser Cys Asp Ala Ser Leu Leu Ser
            20                  25                  30

Ser Asn Ser Gly Leu Ser Ala Ser His Cys Val Asp Gly Ala Leu Pro
        35                  40                  45

Gly Ser Ile Thr Val Ile Ala Gly Leu His Asp Arg Ser Gly Thr Pro
50                  55                  60

Gly Ser Gln Glu Val Asp Ile Thr Gly Tyr Thr Met His Glu Glu Tyr
65                  70                  75                  80

Leu Thr Gly Ile Tyr Thr Tyr Ser Asn Asp Ile Ser Ile Leu Asn Phe
                85                  90                  95

Ala Thr Pro Ile Thr Ile Gly Gly Asn Ile Gln Pro Ala Thr Leu Pro
            100                 105                 110

Ala Asp Asn Ser Asn Asn Tyr Leu Gly Leu Thr Cys Val Ile Ser Gly
        115                 120                 125

Trp Gly Arg Thr Ser Ser Asn Ile Leu Pro Asp Thr Leu Gln Lys
130                 135                 140

Ala Ser Ile Gln Val Ile Gly Thr Asp Glu Cys Gln Thr Leu Val Asp
145                 150                 155                 160

Asn Val Leu Gly Cys Arg Ile Trp Asp Asn His Ile Cys Ile Tyr Asp
                165                 170                 175

Gln Ala Asn Ser Val Gly Ser Cys Asn Gly Asp Ser Gly Gly Pro Leu
            180                 185                 190

Asn Cys Pro Asp Gly Thr Thr Val Ala Gly Ile Thr Ser Trp Gly
        195                 200                 205

Ile Ser Ser Gly Gly Asp Cys Leu Gln Asp Tyr Pro Ser Val Tyr Thr
210                 215                 220

Arg Thr Ser Ala Tyr Leu Asp Trp Ile Ala Ala Asn Thr Pro
225                 230                 235

<210> SEQ ID NO 25
<211> LENGTH: 236
<212> TYPE: PRT
<213> ORGANISM: Eisenia fetida

<400> SEQUENCE: 25

Ile Ile Gly Gly Thr Asp Ala Ser Pro Gly Glu Phe Pro Trp Gln Leu
1               5                   10                  15

Ser Gln Thr Arg Gly Gly Ser His Ser Cys Gly Ala Ser Leu Leu Asn
            20                  25                  30

Ala Leu Asn Gly Leu Ser Ala Gly His Cys Val Asp Gly Ala Leu Pro
        35                  40                  45

Gly Thr Ile Thr Val Ile Ala Gly Leu His Asp Arg Ser Gly Thr Pro
50                  55                  60

```
Gly Ser Gln Glu Val Asp Ile Thr Gly Tyr Thr Val His Glu Glu Tyr
65                  70                  75                  80

Asn Gln Gly Leu Thr Thr Tyr Ala Asn Asp Ile Ser Ile Leu His Phe
                85                  90                  95

Ala Ser Ala Ile Ser Ile Gly Gly Asn Ile Gln Ala Ala Leu Pro
            100                 105                 110

Ala Asn Asn Asn Asp Tyr Asn Gly Leu Thr Cys Val Ile Ser Gly
            115                 120                 125

Trp Gly Arg Thr Gly Ser Ser Asn Val Leu Pro Asp Thr Leu Gln Lys
            130                 135                 140

Ala Ser Ile Gln Val Ile Gly Thr Ala Gln Cys Gln Asn Leu Val Asp
145                 150                 155                 160

Gly Ile Gly Arg Ile Trp Glu Asn His Ile Cys Leu Tyr Asp Ser Ala
                165                 170                 175

Asn Asn Val Gly Ser Cys Asn Gly Asp Ser Gly Gly Pro Leu Asn Cys
            180                 185                 190

Pro Asp Gly Gly Thr Val Val Ala Gly Val Thr Ser Trp Gly Val Ser
            195                 200                 205

Ser Ala Leu Gly Asn Cys Leu Gln Glu Tyr Pro Ser Val Tyr Thr Arg
210                 215                 220

Thr Ser Ala Tyr Leu Ala Trp Ile Ala Asn Asn Ser
225                 230                 235

<210> SEQ ID NO 26
<211> LENGTH: 236
<212> TYPE: PRT
<213> ORGANISM: Lumbricus rubellus

<400> SEQUENCE: 26

Ile Ile Gly Gly Ser Asn Ala Ser Pro Gly Glu Phe Pro Trp Gln Leu
1               5                   10                  15

Ser Gln Thr Arg Gly Gly Ser His Ser Cys Gly Ala Ser Leu Leu Asn
                20                  25                  30

Ala Leu Asn Gly Leu Ser Ala Phe His Cys Val Asp Gly Ala Ala Pro
            35                  40                  45

Gly Thr Ile Thr Val Ile Ala Gly Leu His Asp Arg Ser Gly Thr Pro
50                  55                  60

Gly Ser Gln Glu Val Asp Ile Thr Gly Tyr Thr Met His Glu Asn Tyr
65                  70                  75                  80

Asn Gln Gly Thr Asn Thr Tyr Ala Asn Asp Ile Ala Ile Leu His Phe
                85                  90                  95

Ala Ser Ala Ile Asn Ile Gly Gly Asn Gly Gln Ala Ala Leu Leu Pro
            100                 105                 110

Ala Asn Asn Asp Asn Asp Tyr Ser Gly Leu Thr Cys Val Ile Ser Gly
            115                 120                 125

Trp Gly Arg Lys Gly Ser Ser Asn Val Leu Pro Asp Thr Leu Gln Lys
            130                 135                 140

Ala Ser Ile Gln Val Ile Gly Thr Thr Gln Cys Gln Ser Leu Met Gly
145                 150                 155                 160

Ser Ile Gly His Ile Trp Asp Asn His Ile Cys Leu Tyr Asn Asn Thr
                165                 170                 175

Asn Asn Val Gly Ser Cys Asn Gly Asp Ser Gly Gly Pro Leu Asn Cys
            180                 185                 190

Pro Asp Gly Gly Thr Arg Val Ala Gly Val Thr Ser Trp Gly Val Ser
            195                 200                 205
```

```
Ser Gly Ala Gly Asn Cys Leu Gln Thr Tyr Pro Thr Val Tyr Thr Arg
    210                 215                 220

Thr Ser Ala Tyr Leu Ser Trp Ile Ala Asn Asn Ser
225                 230                 235

<210> SEQ ID NO 27
<211> LENGTH: 238
<212> TYPE: PRT
<213> ORGANISM: Lumbricus rubellus

<400> SEQUENCE: 27

Val Ile Gly Gly Thr Asp Ala Ala Pro Gly Glu Phe Pro Trp Gln Leu
1               5                   10                  15

Ser Gln Thr Arg Gly Gly Ser His Ser Cys Gly Ala Ser Leu Leu Ser
                20                  25                  30

Ser Asn Ser Gly Leu Ser Ala Ser His Cys Val Asp Gly Ala Leu Pro
            35                  40                  45

Gly Ser Ile Thr Val Ile Ala Gly Leu His Asp Arg Ser Gly Thr Pro
50                  55                  60

Gly Ser Gln Glu Val Asp Ile Thr Gly Tyr Thr Met His Glu Glu Tyr
65                  70                  75                  80

Leu Thr Gly Ile Tyr Thr Tyr Ser Asn Asp Ile Ser Ile Leu Asn Phe
                85                  90                  95

Ala Thr Pro Ile Thr Ile Gly Gly Asn Ile Gln Pro Ala Thr Leu Pro
            100                 105                 110

Ala Asp Asn Ser Asn Asn Tyr Leu Gly Leu Thr Cys Val Ile Ser Gly
        115                 120                 125

Arg Gly Gln Thr Ser Ser Asn Ile Leu Pro Asp Thr Leu Gln Lys
130                 135                 140

Ala Ser Ile Gln Val Ile Gly Thr Asp Glu Cys Gln Thr Leu Val Asp
145                 150                 155                 160

Asn Val Leu Gly Tyr Lys Ile Trp His Asn His Ile Cys Ile Tyr Asn
                165                 170                 175

Gln Thr Asn Ser Val Gly Ser Cys Asn Gly Asp Ser Gly Gly Pro Leu
            180                 185                 190

Asn Cys Pro Asp Gly Thr Thr Val Ala Gly Ile Thr Ser Trp Gly
        195                 200                 205

Ile Ser Ser Gly Gly Asp Cys Leu Gln Asp Tyr Pro Ser Val Tyr Thr
210                 215                 220

Arg Thr Ser Ala Tyr Leu Asp Trp Ile Ala Ala Asn Ser Ser
225                 230                 235

<210> SEQ ID NO 28
<211> LENGTH: 242
<212> TYPE: PRT
<213> ORGANISM: Lumbricus rubellus

<400> SEQUENCE: 28

Val Ile Gly Gly Thr Asn Ala Ser Pro Gly Glu Phe Pro Trp Gln Leu
1               5                   10                  15

Ser Gln Gln Arg Gln Ser Gly Ser Trp Ser His Ser Cys Gly Ala Ser
                20                  25                  30

Leu Leu Ser Ser Thr Ser Ala Leu Ser Ala Ser His Cys Val Asp Gly
            35                  40                  45

Val Leu Pro Asn Asn Ile Arg Val Ile Ala Gly Leu Trp Gln Gln Ser
50                  55                  60
```

```
Glu Thr Ser Gly Thr Gln Thr Ala Asn Val Asp Ser Tyr Thr Met His
 65                  70                  75                  80

Glu Asn Tyr Gly Ala Gly Thr Ala Ser Tyr Ser Asn Asp Ile Ala Ile
                 85                  90                  95

Leu His Leu Ala Thr Ser Ile Ser Leu Gly Arg Asn Ile Gln Ala Ala
            100                 105                 110

Val Leu Pro Ala Asn Asn Asn Asp Tyr Ala Gly Thr Thr Cys Val
        115                 120                 125

Ile Ser Gly Trp Gly Arg Thr Asp Gly Thr Asn Asn Pro Pro Asp Ile
    130                 135                 140

Leu Gln Lys Ser Ser Ile Pro Val Ile Thr Thr Ala Gln Cys Thr Ala
145                 150                 155                 160

Ala Met Val Gly Val Gly Gly Ala Asn Ile Trp Asp Asn His Ile Cys
                165                 170                 175

Val Gln Asp Pro Ala Gly Asn Thr Gly Ala Cys Asn Gly Asp Ser Gly
            180                 185                 190

Gly Pro Leu Asn Cys Pro Asp Gly Gly Thr Arg Val Val Gly Val Thr
        195                 200                 205

Ser Trp Val Val Ser Ser Gly Leu Gly Ala Cys Leu Pro Asp Tyr Pro
210                 215                 220

Ser Val Tyr Thr Arg Val Arg Ala Tyr Leu Gly Trp Ile Gly Asp Asn
225                 230                 235                 240

Ser Arg

<210> SEQ ID NO 29
<211> LENGTH: 225
<212> TYPE: PRT
<213> ORGANISM: Lumbricus rubellus

<400> SEQUENCE: 29

Val Val Gly Gly Ser Asp Thr Thr Ile Gly Gln Tyr Pro His Gln Leu
 1               5                  10                  15

Ser Leu Arg Val Thr Gly Ser His Ser Cys Gly Ala Ser Leu Ile Gly
             20                  25                  30

Thr Thr Arg Ala Val Thr Ala Ala His Cys Thr Gly Ser Ala Ile Gly
         35                  40                  45

Val Tyr Thr Ile Leu Gly Gly Thr Thr Asp Arg Thr Val Thr Asn Cys
     50                  55                  60

Ala Thr Cys Val Leu Arg Asp Leu Asn Phe Leu Asn Arg His Pro Gln
 65                  70                  75                  80

Tyr Asp Glu Asn Gly Asn Gly Tyr Pro Asn Asp Val Ala Val Ile Gly
                 85                  90                  95

Phe Ala Ala Val Ala Thr Asn Thr Asn Leu Gln Thr Ile Ser Leu Ala
            100                 105                 110

Thr Pro Ser Asp Gly Ser Phe Ala Gly Asp Thr Gly Val Ile Thr Gly
        115                 120                 125

Trp Gly Lys Thr Ala Ser Ile Gly Gly Ile Pro Asp Ile Leu Gln Met
    130                 135                 140

Ala Thr Met Asn Val Ile Thr Asn Ala Asp Cys Ala Gly Thr Trp Gly
145                 150                 155                 160

Ala Leu Ser Ile Asn Asp Gly His Ile Cys Val Ser Ala Val Gly Arg
                165                 170                 175

Ser Ala Cys Ser Gly Asp Ser Gly Gly Pro Leu Glu Cys Gly Asn Thr
            180                 185                 190
```

-continued

```
Leu Ala Gly Ala Thr Ser Trp Gly Gln Ala Ser Cys Asp Pro Ser Tyr
        195                 200                 205

Pro Ser Val Tyr Thr Arg Ile Ser Tyr Phe Tyr Ser Trp Ile Ile Ala
    210                 215                 220

Gln
225
```